(12) United States Patent
Kawae et al.

(10) Patent No.: US 10,143,442 B2
(45) Date of Patent: Dec. 4, 2018

(54) ULTRASONIC DIAGNOSIS APPARATUS

(71) Applicant: GE MEDICAL SYSTEMS GLOBAL TECHNOLOGY COMPANY, LLC, Waukesha, WI (US)

(72) Inventors: Sotaro Kawae, Tokyo (JP); Shunichiro Tanigawa, Tokyo (JP); Eigil Samset, Horten (NO); Michael Charles MacDonald, Wauwatosa, WI (US)

(73) Assignee: GE Medical Systems Global Technology, LLC, Waukesha, WI (US)

( * ) Notice: Subject to any disclaimer, the term of this patent is extended or adjusted under 35 U.S.C. 154(b) by 1054 days.

(21) Appl. No.: 14/230,842

(22) Filed: Mar. 31, 2014

(65) Prior Publication Data
US 2015/0119710 A1    Apr. 30, 2015

(30) Foreign Application Priority Data

Oct. 24, 2013    (JP) .................................. 2013-221254

(51) Int. Cl.
*A61B 8/00* (2006.01)
*A61B 8/08* (2006.01)
(Continued)

(52) U.S. Cl.
CPC ............... *A61B 8/485* (2013.01); *A61B 8/06* (2013.01); *A61B 8/085* (2013.01); *A61B 8/14* (2013.01);
(Continued)

(58) Field of Classification Search
CPC .................. A61B 8/085; A61B 8/5223; A61B 2018/00577
See application file for complete search history.

(56) References Cited

U.S. PATENT DOCUMENTS

| 5,924,991 A | * | 7/1999 | Hossack | ................. A61B 8/14 128/916 |
| 6,511,427 B1 | * | 1/2003 | Sliwa, Jr. | ............. A61B 5/4869 600/438 |

(Continued)

FOREIGN PATENT DOCUMENTS

| JP | 2006142007 A | 6/2006 |
| JP | 2008-126079 | 6/2008 |

(Continued)

OTHER PUBLICATIONS

Notice of Allowance issued in connection with corresponding KR Application No. 10-2014-0145322 dated Apr. 27, 2017.

(Continued)

*Primary Examiner* — Baisakhi Roy

(57) ABSTRACT

An ultrasonic diagnosis apparatus is provided. The ultrasonic diagnosis apparatus includes an ultrasonic probe configured to transmit ultrasonic push pulses to a biological tissue of a test object and further configured to transmit measuring ultrasonic pulses to the biological tissue subjected to the transmitted push pulses in order to measure an elasticity of the biological tissue, a respiration detection part configured to detect respiration of the test object, and a notification part which, based on the detection by the respiration detection part, is configured to give notification allowing a transmission timing of the push pulses to be recognized.

5 Claims, 39 Drawing Sheets

(51) Int. Cl.
*A61B 8/14* (2006.01)
*A61B 8/06* (2006.01)

(52) U.S. Cl.
CPC .......... *A61B 8/5207* (2013.01); *A61B 8/5223* (2013.01); *A61B 8/543* (2013.01); *A61B 8/5276* (2013.01)

(56) References Cited

U.S. PATENT DOCUMENTS

| | | |
|---|---|---|
| 7,833,221 B2 | 11/2010 | Voegele et al. |
| 8,147,410 B2 | 4/2012 | Zheng |
| 8,235,898 B2 | 8/2012 | Bae et al. |
| 8,353,831 B2 | 1/2013 | Matsumura |
| 8,469,891 B2 | 6/2013 | Maleke et al. |
| 8,545,410 B2 | 10/2013 | Simpson et al. |
| 2003/0204141 A1* | 10/2003 | Nock ............... A61M 37/0092 600/439 |
| 2004/0167403 A1* | 8/2004 | Nightingale ......... A61B 5/0053 600/437 |
| 2005/0215899 A1* | 9/2005 | Trahey ................ A61B 5/0048 600/439 |
| 2007/0093716 A1* | 4/2007 | Radulescu ............... A61B 8/08 600/437 |
| 2011/0137169 A1 | 6/2011 | Akaki et al. |
| 2012/0065507 A1* | 3/2012 | Brunke .................. A61B 8/12 600/442 |
| 2012/0123262 A1* | 5/2012 | Xie ...................... A61B 5/0048 600/438 |
| 2013/0066204 A1* | 3/2013 | Fan ..................... A61B 8/0858 600/438 |
| 2013/0096597 A1* | 4/2013 | Anand ................. A61B 8/4488 606/169 |
| 2013/0317362 A1* | 11/2013 | Shi ....................... A61B 5/0051 600/438 |
| 2014/0018679 A1* | 1/2014 | Chen ...................... A61B 8/085 600/438 |
| 2014/0051998 A1 | 2/2014 | Shimazaki |
| 2016/0000398 A1* | 1/2016 | Raju ....................... A61B 8/06 600/443 |

FOREIGN PATENT DOCUMENTS

| | | |
|---|---|---|
| JP | 2011139896 A | 7/2011 |
| JP | 2012-100997 | 5/2012 |
| JP | 2012170823 A | 9/2012 |

OTHER PUBLICATIONS

Office Action issued in connection with corresponding JP Application No. 2014-167863 dated Mar. 27, 2018.

* cited by examiner

ULTRASONIC DIAGNOSIS APPARATUS

CROSS REFERENCE TO RELATED APPLICATIONS

This application claims the benefit of Japanese Patent Application No. 2013-221254 filed Oct. 24, 2013, which is hereby incorporated by reference in its entirety.

BACKGROUND

The present invention relates to an ultrasonic diagnosis apparatus for measuring the elasticity of biological tissues by sending ultrasonic push pulses thereto.

There are known elasticity measuring techniques for measuring the elasticity of biological tissues by transmitting ultrasonic pulses of high sound pressure (push pulses) thereto from an ultrasonic probe (e.g., see Japanese Unexamined Patent Publication No. 2012-100997). A typical measuring technique that utilizes the push pulses involves using an echo signal of measuring ultrasonic pulses to detect a propagation velocity of shear waves generated by vibration of the biological tissue subject to the push pulses, the detected propagation velocity being used as the basis for calculating an elasticity coefficient of the biological tissue in question. Another elasticity measuring technique utilizing the push pulses is one which calculates position information about the biological tissue using the echo signal of measuring ultrasonic pulses, the position information being used to calculate a displacement of the biological tissue induced by transmission of the push pulses.

In some cases where the above-mentioned elasticity measuring techniques are applied, the same location of the tissue is measured a number of times for elasticity so that an average of such measurements is presented as the final measured value. In such cases, if the biological tissue is moved by respiration, the location being measured is shifted, which renders the measuring of the same location difficult. To avoid such difficulty, the test object is asked to stop breathing for measurement purposes. However, it is sometimes difficult for the test object to keep stopping his or her respiration.

The biological tissue may also be moved by heartbeats or by the test object's movement. Furthermore, the biological tissue may remain still but the position and angle of the ultrasonic probe may change during measurement, which also makes it difficult to obtain accurate measured values of the elasticity of the biological tissue.

On the basis of data about the measured values of the elasticity of the biological tissue of interest (elasticity data), there also are cases where a two-dimensional elasticity image of the biological tissue is displayed in colors reflecting the elasticity data. If the biological tissue is moved or the ultrasonic probe is shifted in such cases, the echo signal obtained from the tissue contains noise. Thus when the biological tissue is moved, accurate elasticity data cannot be obtained and the S/N ratio of the elasticity image above worsens.

BRIEF DESCRIPTION

In a first aspect, an ultrasonic diagnosis apparatus is provided. The ultrasonic diagnosis apparatus includes an ultrasonic probe which transmits ultrasonic push pulses to a biological tissue of a test object and further transmits measuring ultrasonic pulses to the biological tissue subjected to the transmitted push pulses in order to measure the elasticity of the biological tissue, a respiration detection part which detects respiration of the test object, and a notification part which, based on the detection by the respiration detection part, gives notification allowing the transmission timing of the push pulses to be recognized.

In a second aspect, an ultrasonic diagnosis apparatus is provided. The ultrasonic diagnosis apparatus includes an ultrasonic probe which transmits ultrasonic push pulses to a biological tissue of a test object and further transmits measuring ultrasonic pulses to the biological tissue subjected to the transmitted push pulses in order to measure the elasticity of the biological tissue, a respiration detection part which detects respiration of the test object, and a control part which, based on the detection by the respiration detection part, performs control to transmit the push pulses at the timing at which a respiration-induced movement of the biological tissue is minimal.

In a third aspect, an ultrasonic diagnosis apparatus is provided. The ultrasonic diagnosis apparatus includes an ultrasonic probe which transmits ultrasonic push pulses, transmits measuring ultrasonic pulses for measuring the elasticity of a biological tissue of a test object subjected to the transmitted push pulses, and transmits ultrasonic pulses for detecting a movement of the biological tissue, and a processor which executes a program to implement a movement detection function for detecting the movement of the biological tissue based on echo data of the ultrasonic pulses for biological tissue movement detection, and a notification function for giving notification allowing the transmission timing of the push pulses to be recognized on the basis of the detection by the movement detection function.

In a fourth aspect, an ultrasonic diagnosis apparatus is provided. The ultrasonic diagnosis apparatus includes an ultrasonic probe which transmits ultrasonic push pulses, transmits measuring ultrasonic pulses for measuring the elasticity of a biological tissue of a test object subjected to the transmitted push pulses, and transmits ultrasonic pulses for detecting a movement of the biological tissue, and a processor which executes a program to implement a movement detection function for detecting the movement of the biological tissue based on echo data of the ultrasonic pulses for biological tissue movement detection, and a transmission control function for performing control to transmit the push pulses and the measuring ultrasonic pulses at the timing at which the movement of the biological tissue is minimal on the basis of the detection by the movement detection function.

According to the above-mentioned first aspect, notification is performed to let the transmission timing of the push pulses be recognized on the basis of the detection by the respiration detection part. Thus when the same location of the tissue is measured a number of times for elasticity, the push pulses may be transmitted for elasticity measurement at the timing at which the effects of body movement by respiration are minimal. This makes it possible suitably to measure the same location of the tissue.

According to the above-mentioned second aspect, the push pulses are transmitted at the timing at which the body movement induced by respiration is minimal on the basis of the detection by the respiration detection part. Thus when the same location of the tissue is measured a number of times for elasticity, the push pulses may be transmitted for elasticity measurement at the timing at which the effects of body movement by respiration are minimal. This makes it possible suitably to measure the same location of the tissue.

According to the above-mentioned third aspect, notification is performed to let the transmission timing of the push pulses be recognized on the basis of the detection by the movement detection function. With the movement of the biological tissue and that of the ultrasonic probe inhibited, the push pulses and the measuring ultrasonic pulses may be transmitted so as to obtain the echo signal of the measuring ultrasonic pulses. Accurate elasticity coefficients of the biological tissue can then be obtained based on the echo signal of the measuring ultrasonic pulses. It is also possible to suppress noise in the echo signal.

According to the above-mentioned fourth aspect, the push pulses and the measuring ultrasonic pulses are transmitted at the timing at which the movement of the biological tissue is minimal on the basis of the detection by the movement detection function. With the movement of the biological tissue and that of the ultrasonic probe thus inhibited, the echo signal of the measuring ultrasonic pulses can be obtained. As a result, accurate elasticity coefficients of the biological tissue can be acquired based on the echo signal of the measuring ultrasonic pulses. It is also possible to suppress noise in the echo signal.

DETAILED DESCRIPTION

Figure 1:
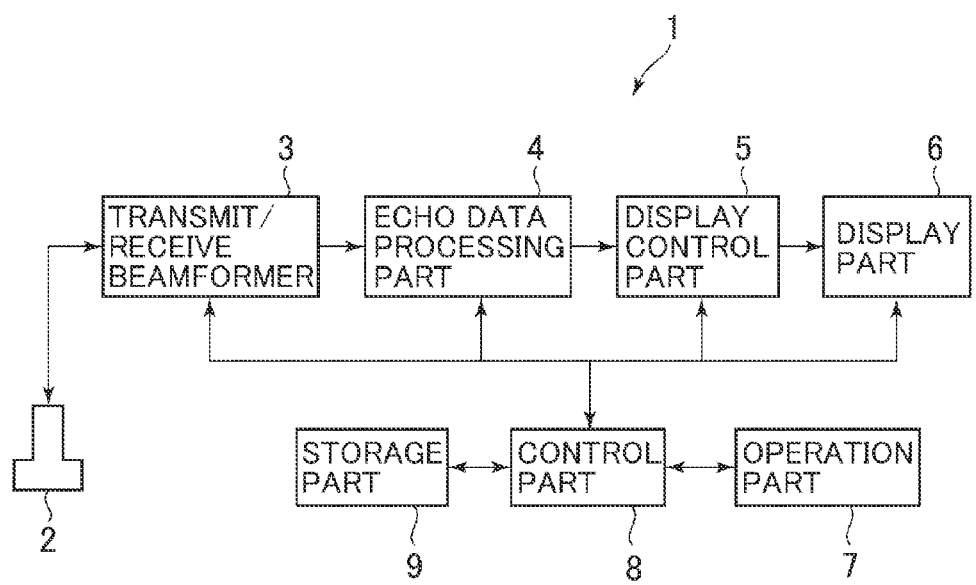
FIG. 1 is a block diagram showing an overall configuration of an exemplary ultrasonic diagnosis apparatus.

Exemplary embodiments will now be described below with reference to the accompanying drawings.

First Embodiment

The first embodiment is explained first. An ultrasonic diagnosis apparatus 1 shown in FIG. 1 includes an ultrasonic probe 2, a transmit/receive beamformer 3, an echo data processing part 4, a display control part 5, a display part 6, an operation part 7, a control part 8, and a storage part 9.

The ultrasonic probe 2 transmits ultrasonic weaves to a biological tissue of a test object. This ultrasonic probe 2 transmits ultrasonic pulses (push pulses) to the biological tissue to generate shear waves therein. The ultrasonic probe 2 also transmits measuring ultrasonic pulses for measuring a propagation velocity of the shear waves and receives an echo signal of the transmitted measuring ultrasonic pulses. The ultrasonic probe 2 further transmits imaging ultrasonic waves for generating an ultrasonic image such as a B-mode image and receives an echo signal of the transmitted imaging ultrasonic waves. The ultrasonic probe 2 is an example of the ultrasonic probe.

On the basis of a control signal from the control part 8, the transmit/receive beamformer 3 drives the ultrasonic probe 2 to transmit the above-mentioned various ultrasonic waves having predetermined transmission parameters. Given an echo signal of the ultrasonic waves, the transmit/receive beamformer 3 performs signal processing such as additional phasing.

Figure 2:
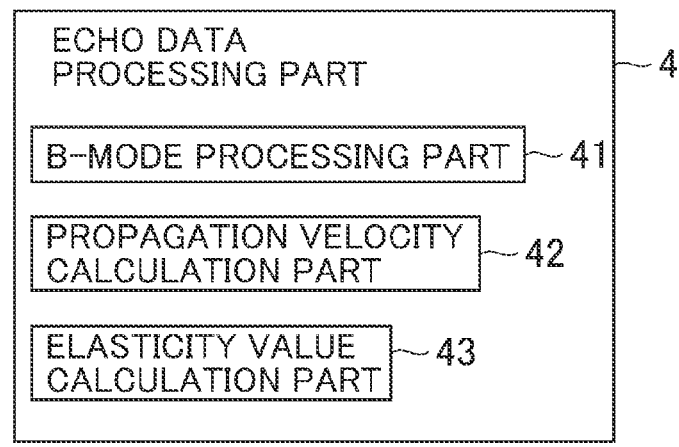
FIG. 2 is a block diagram showing a configuration of an echo data processing part.

As shown in FIG. 2, the echo data processing part 4 has a B-mode processing part 41, a propagation velocity calculation part 42, and an elasticity coefficient calculation part 43. The B-mode processing part 41 generates B-mode data by performing B-mode processing such as logarithmic compression and envelope demodulation on the echo data output from the transmit/receive beamformer 3.

Also, the propagation velocity calculation part 42 calculates the propagation velocity of the shear waves based on the echo data output from the transmit/receive beamformer 3. On the basis of the propagation velocity thus calculated, the elasticity coefficient calculation part 43 calculates the elasticity coefficient of the biological tissue subjected to the transmitted push pulses. The operations involved will be discussed later in detail. The propagation velocity calculation part 42 and the elasticity coefficient calculation part 43 are examples of the elasticity measured value calculation part.

Figure 3:
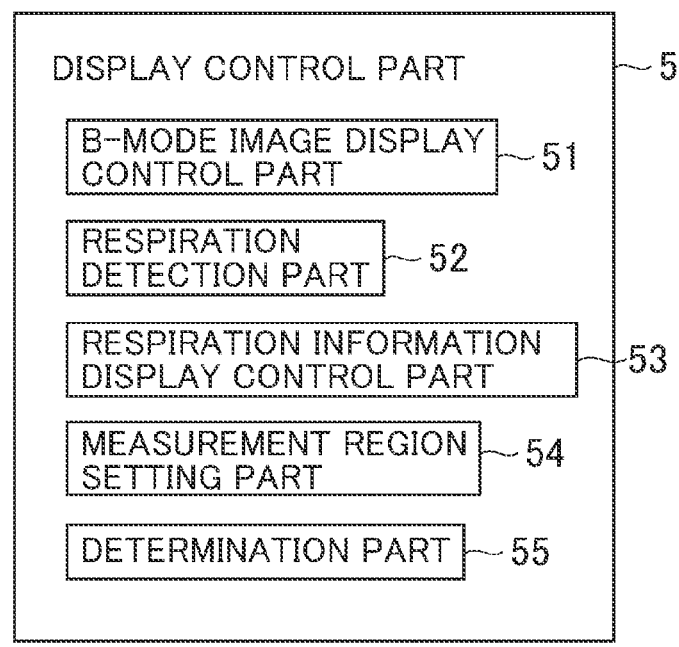
FIG. 3 is a block diagram showing a configuration of a display control part in a first embodiment.

As shown in FIG. 3, the display control part 5 has a B-mode image display control part 51, a respiration detection part 52, a respiration information display control part 53, a measurement region setting part 54, and a determination part 55. The B-mode image display control part 51 generates B-mode image data by scan-converting the B-mode data using a scan converter. Also, the B-mode image display control part 51 causes the display part 6 to display a B-mode image based on the B-mode image data.

The respiration detection part 52 detects the respiration of the test object on the basis of the B-mode image data. Specifically, the respiration detection part 52 detects a respiration-induced movement of the biological tissue through tracking by pattern matching involving correlation calculations targeted on the B-mode image data.

The respiration information display control part 53 generates respiration information about the test object on the basis of the movement of the biological tissue detected by the respiration detection part 52, and causes the display part 6 to display a waveform indicative of a chronological change in the generated respiration information. The operations involved will be discussed later in detail.

Based on the input performed by an operator through the operation part 7, the measurement region setting part 54 sets in the B-mode image the region that is subject to elasticity measurement utilizing the push pulses.

On the basis of the respiration information, the determination part 55 determines whether it is time to measure elasticity by use of the push pulses. The operations involved will be discussed later in detail.

The display part 6 may be a liquid crystal display (LCD) or an organic electroluminescence (El) display, for example. The display part 6 that displays waveforms indicative of the chronological change in the respiration information is an example of the notification part.

The operation part 7 is configured to include a pointing device such as a keyboard and a trackball, not shown, which are operated by the operator to input instructions and information.

The control part 8 is a processor such as a CPU (central processing unit). The control part 8 reads programs from the storage part 9 and thereby performs the functions of the components constituting the ultrasonic diagnosis apparatus 1. For example, the control part 8 retrieves the programs stored in the storage part 9 and, based on the retrieved programs, performs the functions of the transmit/receive beamformer 3, echo data processing part 4, and display control part 5.

Using the programs, the control part 8 may perform part or all of the functions of the transmit/receive beamformer 3, of the functions of the echo data processing part 4, and of the functions of the display control part 5. If the control part 8 carries out only part of the functions involved, the remaining functions may be performed by hardware such as circuits.

Incidentally, the functions of the transmit/receive beamformer 3, echo data processing part 4, and display control part 5 may also be implemented by hardware such as circuits.

The storage device 9 is an HDD (hard disk drive) or a semiconductor memory such as a RAM (random access memory) or a ROM (read only memory).

Figure 4:
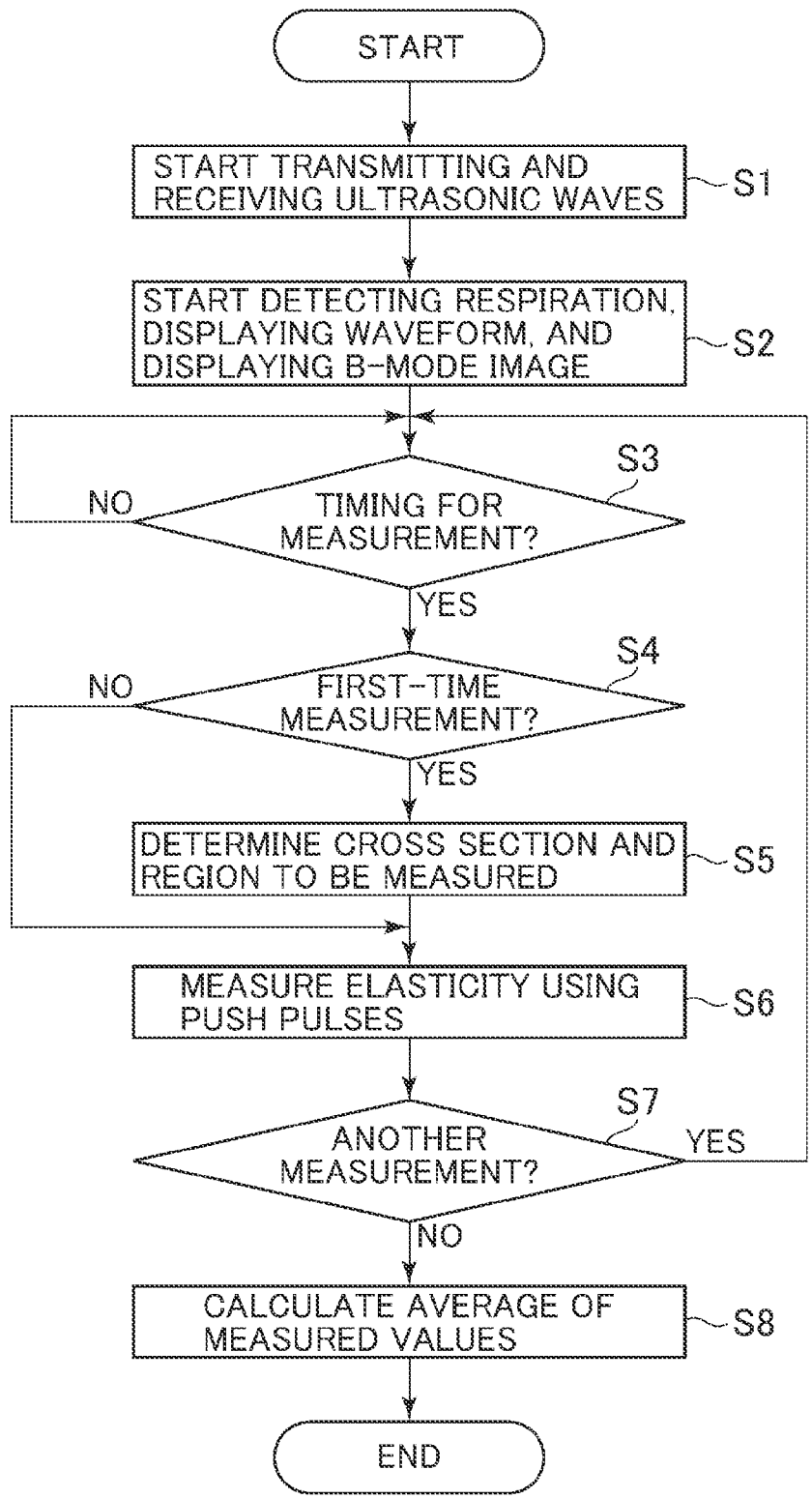
FIG. 4 is a flowchart showing a processing flow of the ultrasonic diagnosis apparatus in the first embodiment.

Explained next based on the flowchart of FIG. 4 is a processing flow in which this ultrasonic diagnosis apparatus 1 measures the elasticity of a biological tissue using push pulses. First in step S1, the operator causes the ultrasonic probe 2 to start transmitting and receiving ultrasonic waves to and from the target for elasticity measurement in the test object. For example, the target for elasticity measurement is the liver of the test object.

Figure 5:
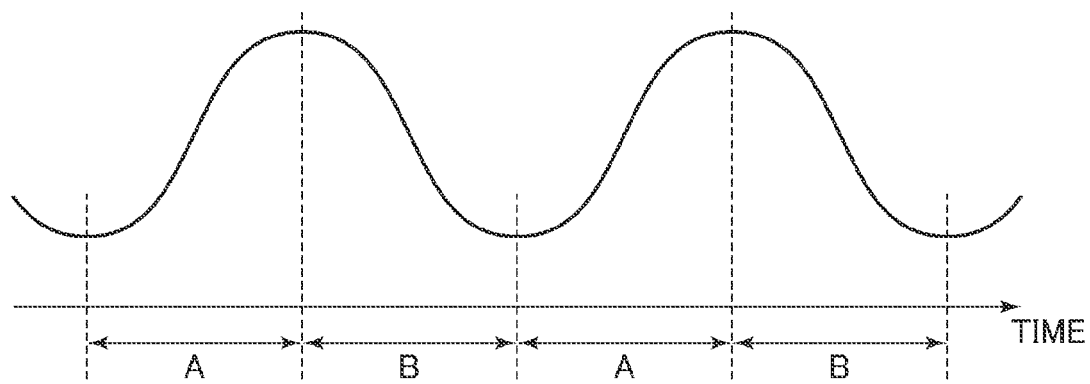
FIG. 5 is an explanatory drawing for explaining respiration information.

Next in step S2, B-mode image data is generated on the basis of the echo signal obtained from the transmission and reception of the ultrasonic waves. Based on the B-mode image data thus generated, the respiration detection part 52 starts detecting respiration of the test object. Also in step S2, the respiration information display control part 53 generates respiration information about the test object on the basis of the information detected by the respiration detection part 52. The following is a more specific explanation: upon inhalation, the biological tissue moves in one direction; upon exhalation, the biological tissue moves in a direction opposite to that in effect upon inhalation. On the basis of such movements of the biological tissue, the respiration information display control part 53 generates respiration information such as is shown in FIG. 5. In the respiration information of FIG. 5, the curve is positively sloped (upward-sloping) upon exhalation. Thus the period A in FIG. 5 is an exhalation period. Upon inhalation, the curve is negatively sloped (downward-sloping), so that the period B in FIG. 5 is an inhalation period.

Figure 6:
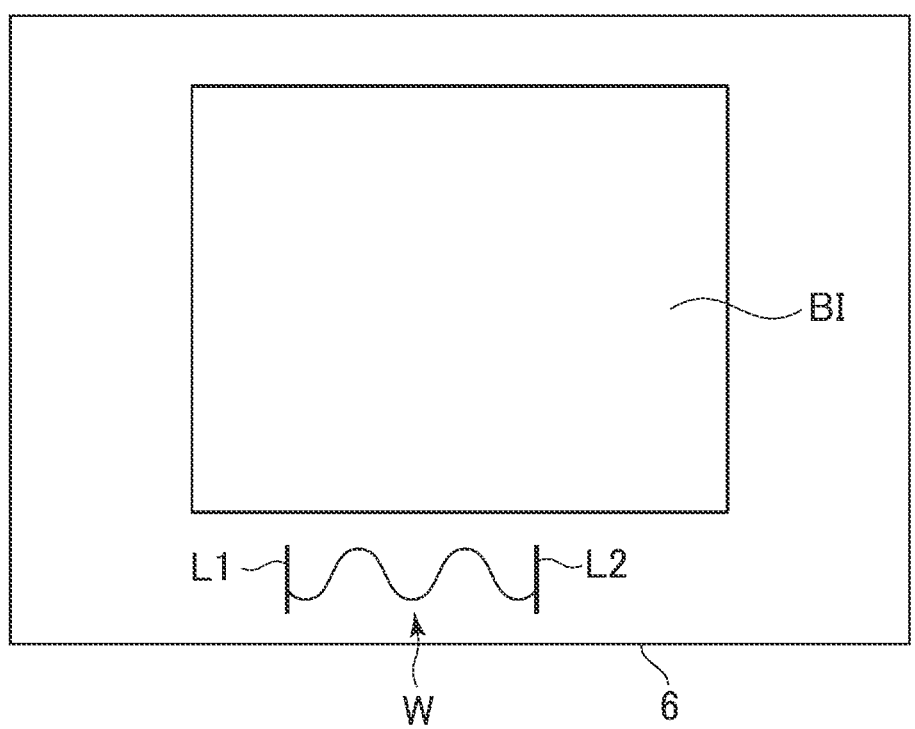
FIG. 6 is a diagram showing a display part displaying a B-mode image.

Also in step S2, as shown in FIG. 6, the display part 6 starts displaying a B-mode image BI in real time based on the B-mode image data. The respiration information display part 53 causes the display part 6 to display a waveform W indicative of a chronological change in the respiration information. The display of the waveform W is an example of the notification performed to let the transmission timing of push pulses be recognized. The waveform W is an example of the image indicative of the chronological change in respiration.

On the display part 6, the waveform W is displayed between lines L1 and L2 extending in the vertical direction. In the waveform W, the rightmost line L2 indicates the respiration information currently in effect. The waveform W shifts in a horizontal direction with the passage of time.

Figure 7:
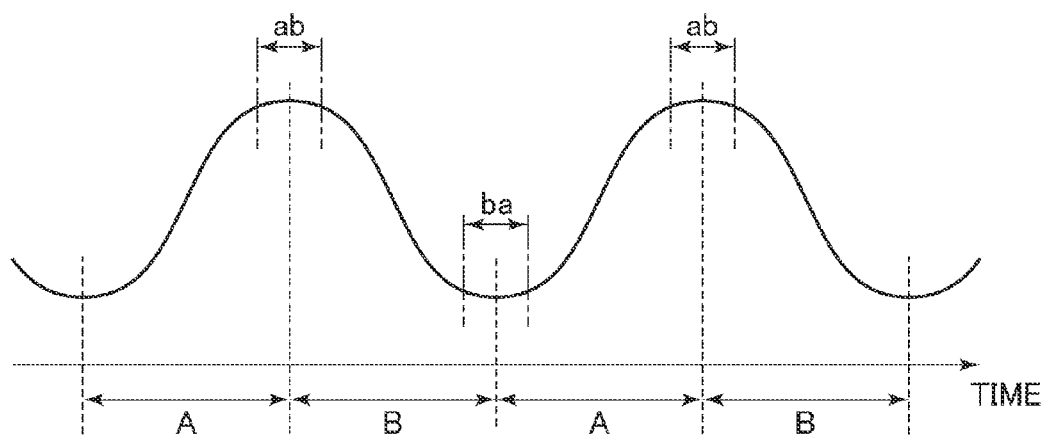
FIG. 7 is an explanatory drawing for explaining the timing for measuring elasticity.

Next in step S3, the operator determines whether it is time to measure elasticity by use of the push pulses. The operator observes the waveform W displayed on the display part 6 and makes the determination based on the observed waveform W. Specifically, given the respiration information shown in FIG. 7, the operator determines that it is time to measure elasticity upon reaching a point in time during a period "ab" where inhalation changes to exhalation or a point in time during a period "ba" where exhalation changes to inhalation. A period "ab" and a period "ba" are periods where the movement of the biological tissue is minimal. For example, when the rightmost edge of the waveform W (position of the line L2 above) shown on the display part 6 reaches the period in which the movement of the biological tissue is minimal, the operator determines that now is the time to measure elasticity.

In the first embodiment, the timing for elasticity measurement is the timing for transmitting the push pulses to measure elasticity. This is the timing at which the respiration-induced movement of the biological tissue is minimal.

Incidentally, the storage part 9 may store beforehand the settings for determining which periods in the respiration information should be established as the above-mentioned periods "ab" and "ba" and which point in time in each of these periods should be set as the timing for measuring elasticity. Alternatively, the operator may establish the settings as desired.

Figure 8:
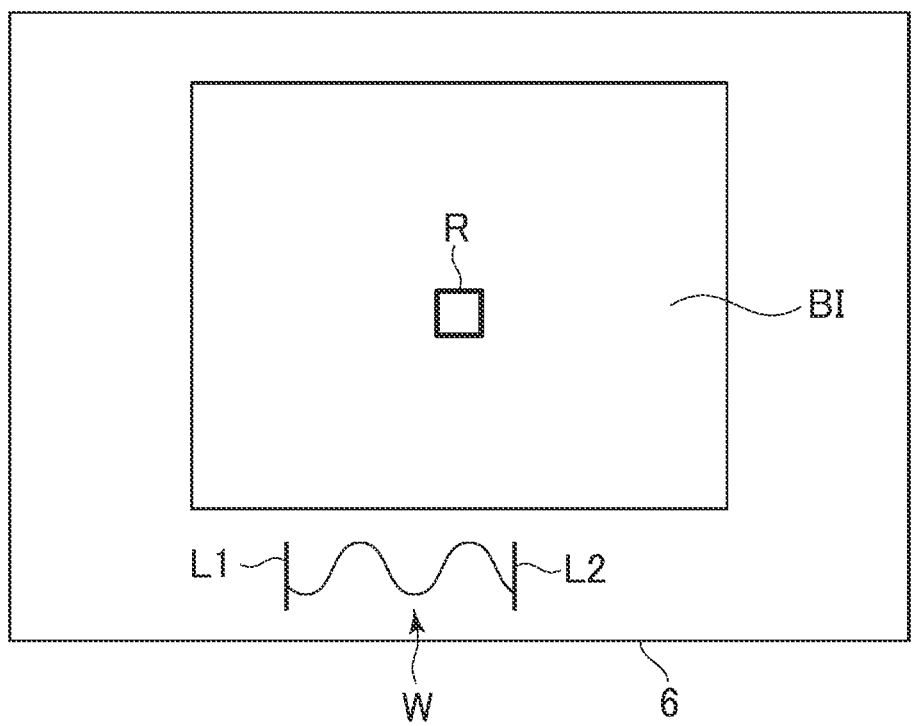
FIG. 8 is a diagram showing a display part on which a measurement region is set in a B-mode image.

If the operator determines in step S3 above that it is not time to make the measurement ("No" in step S3), the operator continues to observe the waveform W. On the other hand, if the operator determines that it is time to perform the measurement ("Yes" in step S3), then control is passed to step S4. In step S4, the control part 8 determines whether this measurement is a first-time measurement. This determination may be carried out alternatively by the operator. If it is determined that this measurement is a first-time measurement ("Yes" in step S4), control is passed to step S5. In step S5, the operator determines the cross section to be measured by adjusting the position and angle of the ultrasonic probe 2. Given a B-mode image BI of this cross section, the operator sets a measurement region R using the operation part 7, as shown in FIG. 8.

Control is passed to step S6 when in step S5 above the cross section to be measured was determined and the measurement region R was set, or when the measurement was not determined to be a first-time measurement in step S4 above ("No" in step 4). In step S6, the measurement region R is measured for elasticity using push pulses. Where the measurement is performed a second or subsequent time, the measurement region R set for the first-time elasticity measurement is measured for elasticity.

Specifically, the operator inputs through the operation part 7 instructions to measure elasticity using the push pulses. In turn, the control part 8 first outputs a signal to the transmit/receive beamformer 3 causing the ultrasonic probe 2 to transmit the push pulses to the biological tissue. The control part 8 then outputs a signal to the transmit/receive beamformer 3 thereby to transmit the measuring ultrasonic pulses for detecting the shear waves induced by the push pulses in the biological tissue and for measuring a propagation velocity of the detected shear waves. The signal causes the ultrasonic probe 2 to transmit the measuring ultrasonic pulses and receive an echo signal of the transmitted ultrasonic pulses. Based on the echo signal thus received, the propagation velocity calculation part 42 calculates the propagation velocity of the shear waves. Also, the elasticity coefficient calculation part 43 calculates an elasticity coefficient (Young's modulus in pascals (Pa)) on the basis of the propagation velocity thus calculated. Alternatively, only the propagation velocity may be calculated while the elasticity coefficient is omitted.

In the first embodiment, the measurement region R is measured for elasticity to obtain the propagation velocity and/or the elasticity coefficient of the point at which the measurement region R has been set. The propagation velocity and the elasticity coefficient above are examples of the measured values of elasticity.

The transmission of the measuring ultrasonic pulses may be carried out not only once but also a number of times corresponding to a single transmission of the push pulses.

It is assumed that the measurement region R is set in step S5 above and elasticity is measured in step S6 above, both in the periods in which the respiration-induced movement of the biological tissue is minimal.

It is the storage part 9 that stores transmission timing information indicating at which point in time of the respiration information the push pulses were transmitted.

Next in step S7, it is determined whether or not to measure elasticity again using the push pulses. In this case, the elasticity measurement is carried out n times (where n is a natural number of at least 2). Thus in step S7, it is determined whether elasticity was measured for the nth time in the preceding step S6. The determination may be performed either by the operator or by the control part 8. Where the operator is to perform the determination, the display part 6 may be arranged to display a message verifying whether the elasticity measurement is to be made again using the push pulses.

Figure 9:
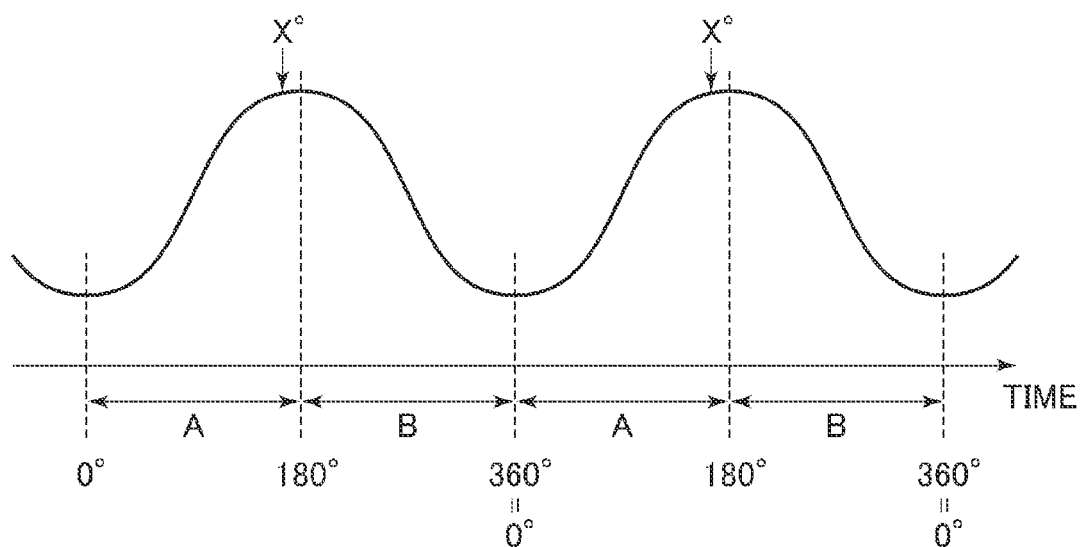
FIG. 9 is a diagram showing the same time phase in one cycle of respiration information.

If it is determined in step S7 above that elasticity is not to be measured again ("No" in step S7), control is passed to step S8. On the other hand, if it is determined in step S7 above to again measure elasticity ("Yes" in step S7), control is returned to step S3. In step S3 at a second or subsequent measurement, the determination part 55 determines whether it is time to measure elasticity based on the transmission timing information. In step S6, the determination part 55 determines whether now is the time to measure elasticity so that the push pulses may be transmitted at the same respiration timing as at the first time. The same respiration timing signifies the same phase in each cycle of respiration information. That is, if each cycle of respiration information is assumed to range from 0° to 360° as shown in FIG. 9 and if the timing for a first-time push pulse transmission is X°, then the timing for elasticity measurement is determined in such a manner that the timing for a second or subsequent push pulse transmission will also take place at X°.

If it is determined in step S3 above that it is time to measure elasticity, control is passed to step S4. In step S4, the control part 8 determines whether this is a first-time measurement. Since the measurement here is not the first-time measurement, this measurement is determined to be a subsequent measurement and control is passed to step S6. In step S6, the control part 8 outputs a signal to the transmit/receive beamformer 3 to transmit the push pulses and measuring ultrasonic pulses as discussed above. The timing for transmitting the push pulses and measuring ultrasonic pulses is the same as that of the first-time transmission. Thus the elasticity measurement for the second or subsequent time is carried out with the push pulses and measuring ultrasonic pulses transmitted automatically at the same timing as the first time.

When the measurement count has reached "n" times, control is passed to step S8. In step S8, an average of the measured values obtained from the "n" measurements is calculated. Specifically, the elasticity coefficient calculation part 43 calculates an average of the elasticity coefficients. Alternatively, the propagation velocity calculation part 42 may calculate an average of the propagation velocities. The average of the elasticity coefficients and that of the propagation velocities above are examples of the values based on the measured values calculated at each of a number of push pulse transmissions.

The averages thus calculated are displayed on the display part 6. Following the calculation of the averages in step S8, the process is brought to an end.

According to the ultrasonic diagnosis apparatus 1 of the first embodiment, the elasticity of the biological tissue is measured at the timing at which the tissue movement is minimal and at the same respiration timing from the first time to the nth time. This makes it possible to measure the same location of the biological tissue from the first time to the nth time without requiring the test object to stop his or her respiration during the measurement. As a result, a more accurate average of the "n" measurements can be obtained. In the second and subsequent elasticity measurements, elasticity can be measured automatically at the same respiration timing set for the first-time elasticity measurement.

Figure 10:
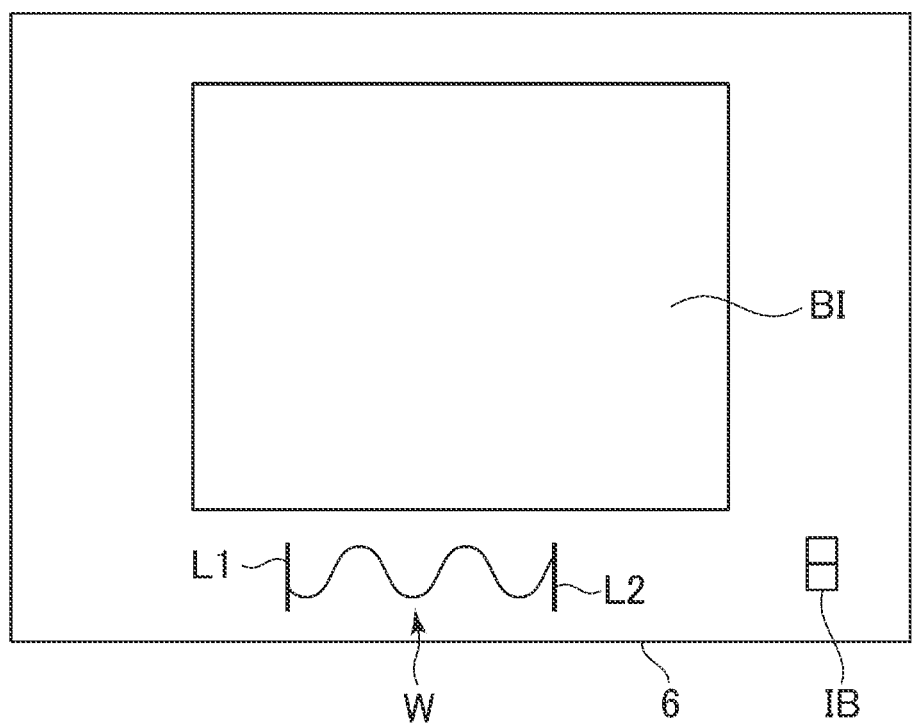
FIG. 10 is a diagram showing a display part displaying an indicator bar along with a respiration information waveform in relation to a first variation of the first embodiment.

What follows is an explanation of variations of the above-described first embodiment. A first variation of the embodiment is explained first. In step S2 above, the respiration information display control part 53 causes the display part 6 to display an indicator indicative of an evaluation of the waveform W and respiration information as shown in FIG. 10. The evaluation in this context refers to an evaluation of how appropriate the timing is for push pulse transmission. With this variation, the indicator is provided as an indicator bar IB.

Figure 11:
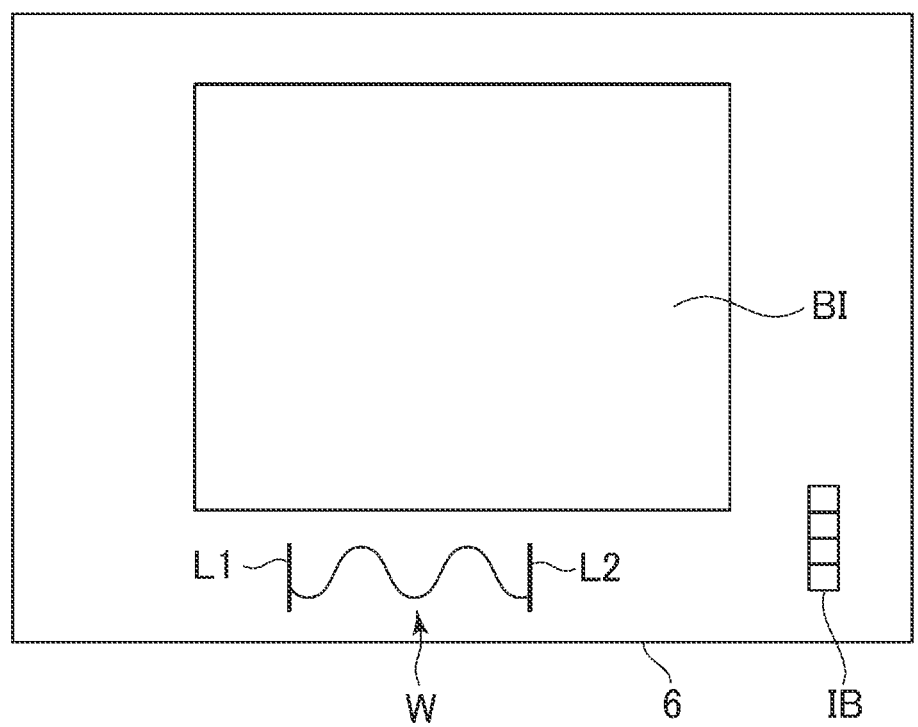
FIG. 11 is a diagram showing a display part displaying an indicator bar along with a respiration information waveform in relation to the first variation of the first embodiment, the indicator bar having a height different from that of the indicator bar in FIG. 10.
Figure 12:
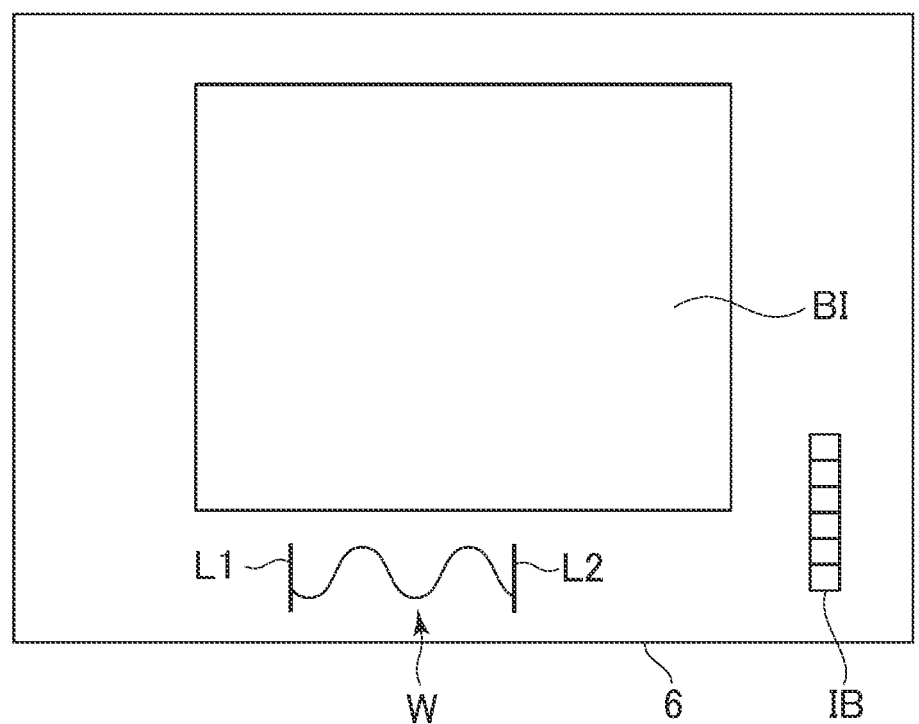
FIG. 12 is a diagram showing a display part displaying an indicator bar along with a respiration information waveform in relation to the first variation of the first embodiment, the indicator bar having a height different from that of the indicator bar in FIG. 10 or in FIG. 11.

The indicator bar IB is explained below. As shown in FIGS. 10 through 12, the indicator bar IB varies in height depending on the change in respiration information. The respiration information display control part 53 divides the respiration information waveform into a number of segments from the viewpoint of the appropriateness of the timing for push pulse transmission, and displays the indicator bar IB having a height corresponding to each of the segments.

Figure 13:
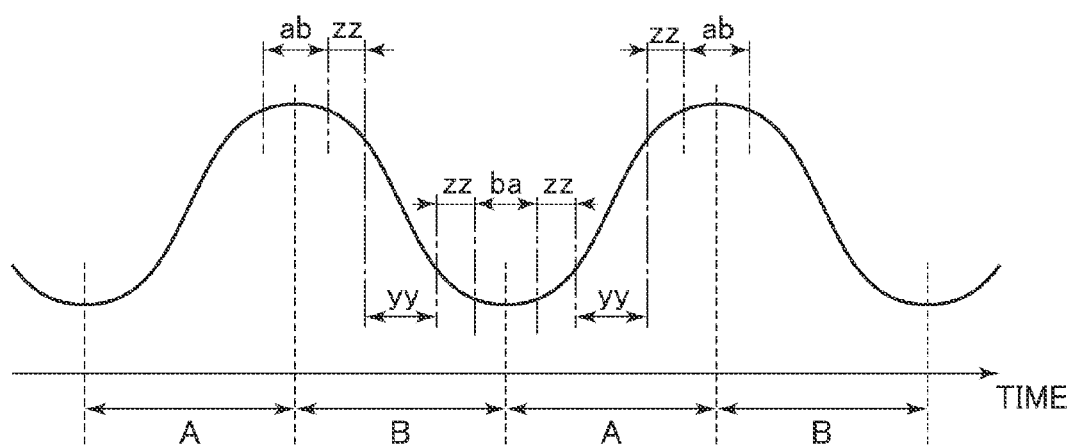
FIG. 13 is a diagram for explaining how the height of the indicator bar is varied with changes in respiration information.

Specifically, in a period "yy" in which there is a steep change in the respiration information as shown in FIG. 13, the indicator bar ID has a minimum height as depicted in FIG. 10. On the other hand, in the period "ab" where inhalation changes to exhalation and in the period "ba" where exhalation changes to inhalation in the respiration information, the indicator bar IB has a maximum height as shown in FIG. 12. In a period "zz" between the period "ab" and the period "yy" as well as between the period "yy" and the period "ba," the indicator bar IB has a height between minimum and maximum as shown in FIG. 11. The indicator bar IB is an example of the image based on the evaluation of respiration information.

The indicator bar IB may be displayed in different colors corresponding to the different bar heights.

In step S3 above, the operator determines that it is time to measure elasticity when the indicator bar IB has the maximum height (the state in FIG. 12). According to the first variation of the first embodiment, the display of the indicator bar IB allows the operator easily to determine whether it is time to measure elasticity.

Figure 14:
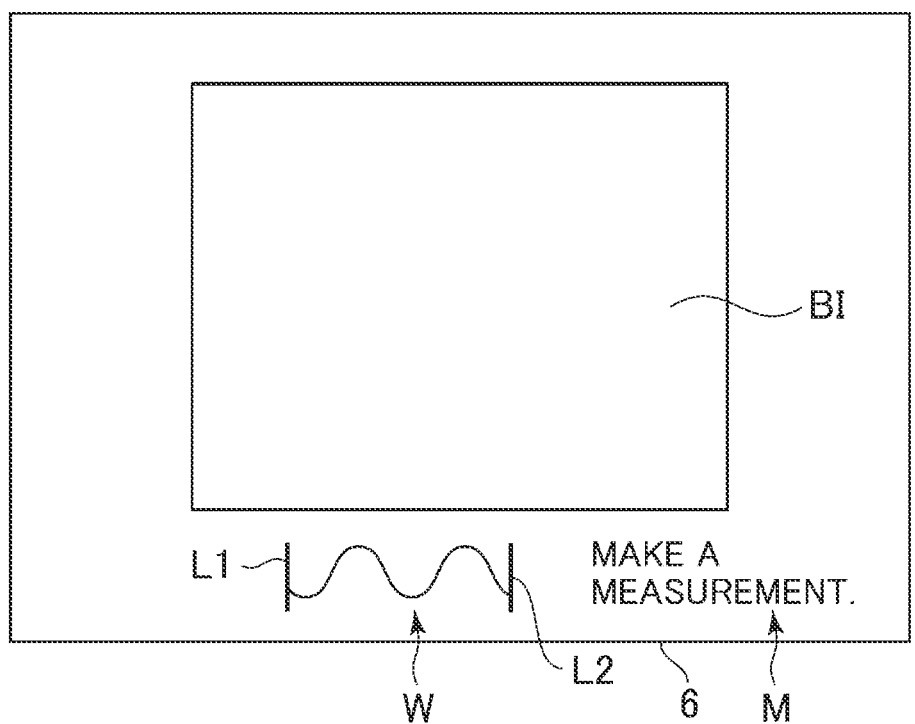
FIG. 14 is a diagram showing a display part displaying a respiration information waveform along with a message indicating that it is time to measure elasticity.

A second variation of the first embodiment is explained next. When the period "ab" or "ba" in the respiration information is reached, the respiration information display control part 53 causes the display part 6 to display a message M indicating that now is the time to measure elasticity, as shown in FIG. 14. The message M allows the operator easily to determine in step S3 above that it is time to measure elasticity. The message M is an example of the image based on the evaluation of respiration information.

A third variation of the first embodiment is explained below. With the first embodiment described above, the operator determines whether it is time to measure elasticity in step S3 for the first-time elasticity measurement. With the third variation of the first embodiment, by contrast, the determination part 55 determines whether it is time to measure elasticity also for the first-time elasticity measurement. Specifically, on the basis of the respiration information, the determination part 55 determines whether this is the timing, to be set, at which the respiration-induced movement of the biological tissue is minimal. For example, the timing, to be set, for the respiration-induced movement of the biological tissue to become minimal is a point in time during the period "ab" above where inhalation changes to exhalation or a point in time during the period "ba" above where exhalation changes to inhalation. The periods "ab" and "ba" can be detected using the gradient of the respiration information at any given point in time. The periods "ab" and "ba" can be detected using the gradient of the respiration information at any given point in time.

With the third variation of the first embodiment, the operator does not perform the determination in step S3. It follows that there is no need to display the waveform W indicative of the chronological change in the respiration information, the indicator bar ID, or the message M.

If in step S3 above the determination part 55 determines that it is time to perform the measurement, control is passed to step S4. In step S4, the control part 8 determines whether the measurement is a first-time measurement. On the other hand, if the determination part 55 determines in step S3 that it is not time to make the measurement, the determination part 55 continues to perform the determination.

In step S5 above, the display part 6 displays a message prompting the operator to set the measurement region R. In response, the operator can determine the cross section to be measured and set the measurement region R accordingly.

When the measurement region R is set in step S5 above, step S6 is reached. In step S6, as explained above, the control part 8 first outputs the signal to the transmit/receive beamformer 3 to transmit the push pulses and then outputs the signal thereto to transmit the measuring ultrasonic pulses.

For the second or subsequent measurement, with the determination part 55 determining in step S4 above that it is time to make the measurement, the control part 8 in step S6 above first outputs the signal to the transmit/receive beamformer 3 for push pulse transmission and then outputs the signal thereto for measuring ultrasonic pulse transmission as discussed above.

According to the third variation of the first embodiment explained above, it is possible automatically to measure elasticity at the timing at which the movement of the biological tissue is minimal and at the same respiration timing from the first time to the nth time.

Figure 15:
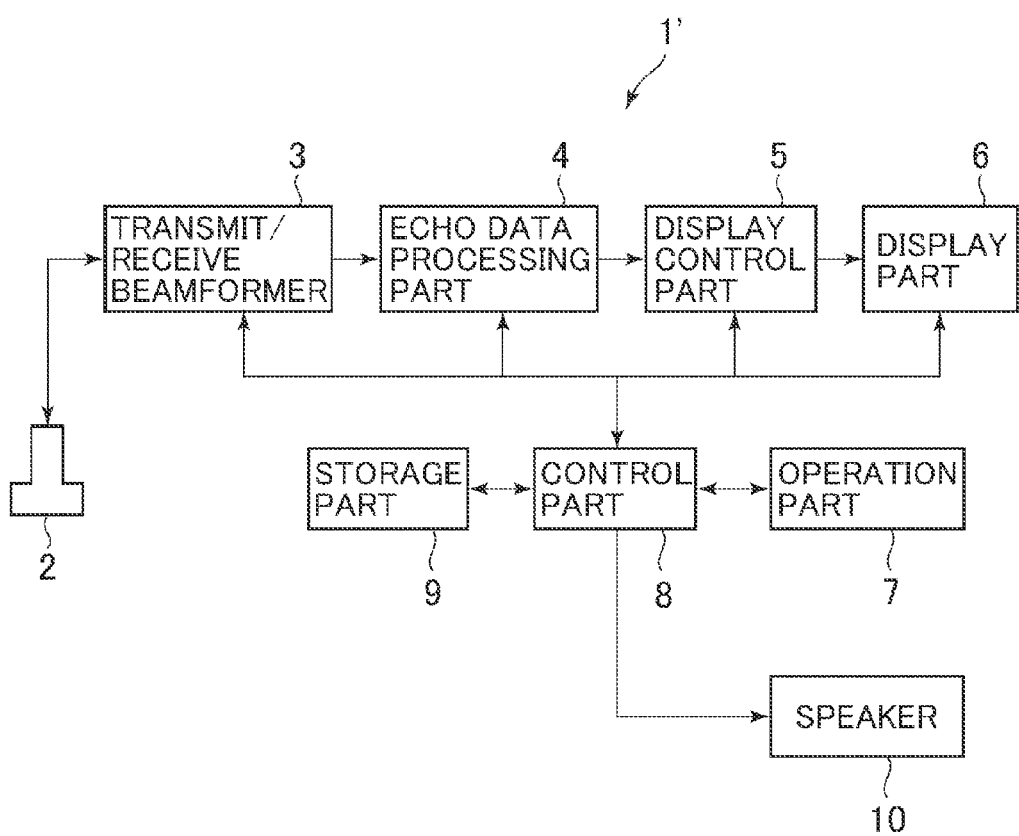
FIG. 15 is a block diagram showing an overall configuration of an ultrasonic diagnosis apparatus as a fourth variation of the first embodiment.

A fourth variation of the first embodiment is explained next. As shown in FIG. 15, an ultrasonic diagnosis apparatus 1' of the fourth variation is furnished with a speaker 10. The speaker 10 is an example of the notification part.

In this variation, the control part 8 causes the speaker 10 to output a sound based on the respiration information detected by the respiration detection part 52. Specifically, when the period "ab" or "ba" above is reached in the respiration information, the control part 8 causes the speaker 10 to output a sound indicating that it is time to measure elasticity. The sound output from the speaker 10 may be a voice message or an alarm sound, for example. The sound from the speaker 10 allows the operator easily to determine that now is the time to measure elasticity.

Figure 16:
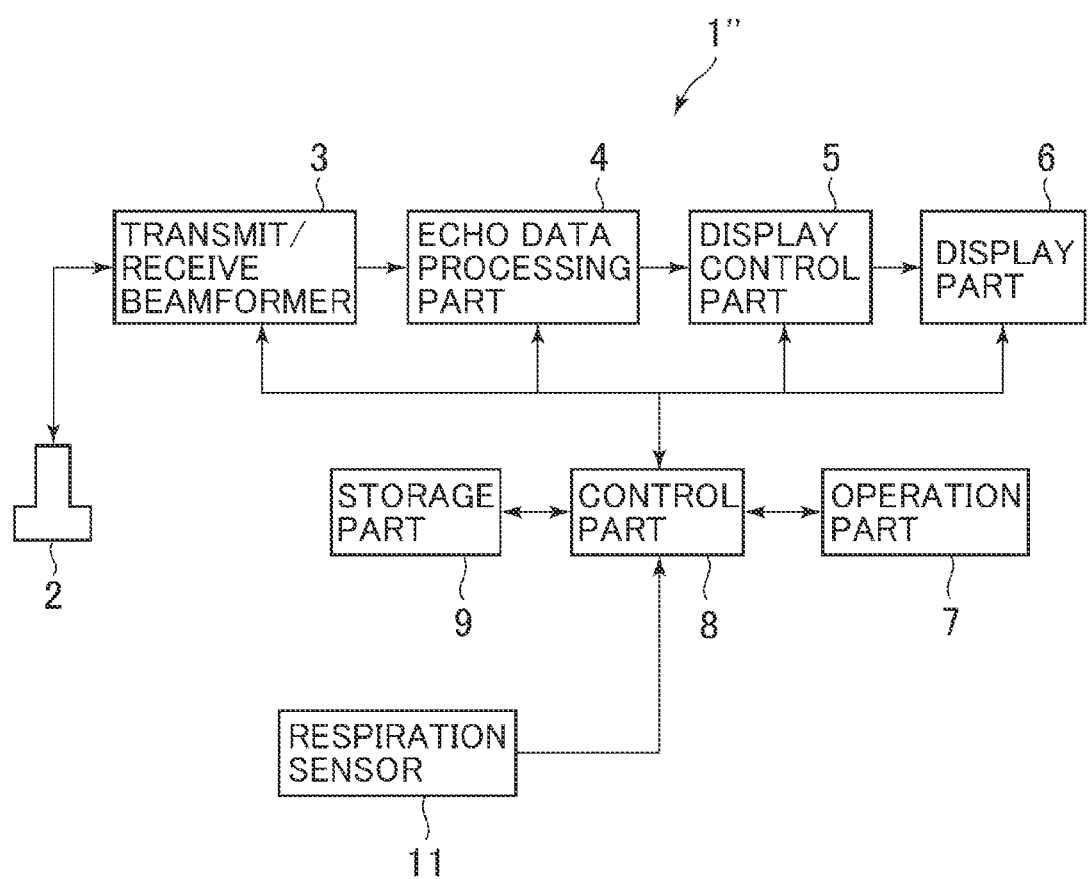
FIG. 16 is a block diagram showing an overall configuration of an ultrasonic diagnosis apparatus as a fifth variation of the first embodiment.

A fifth variation of the first embodiment is explained next. As shown in FIG. 16, an ultrasonic diagnosis apparatus 1" of the fifth variation is furnished with a respiration sensor 11. The respiration sensor 11 is an example of the respiration detection part.

The respiration sensor 11 is attached to the test object and outputs a respiration signal indicative of the test object's respiration movement. The respiration signal is input to the control part 8 which, after processing the input signal, forwards the processed signal as respiration information to the respiration information display control part 53.

Figure 17:
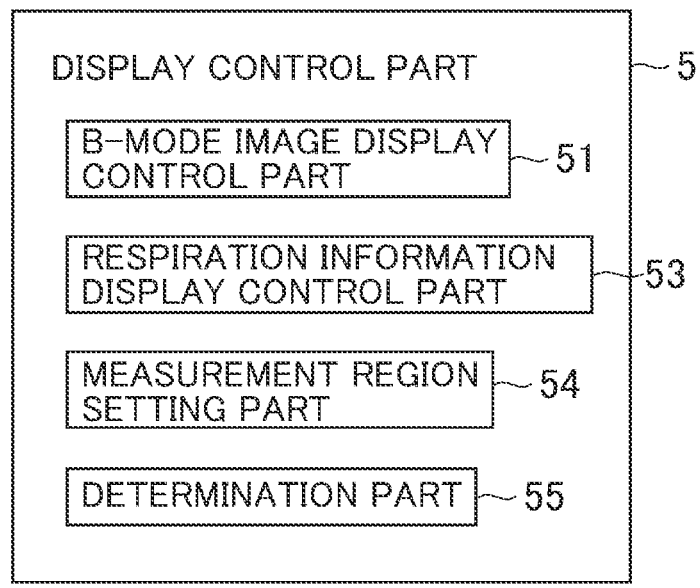
FIG. 17 is a block diagram showing a configuration of a display control part in the fifth variation of the first embodiment.

Since the fifth variation is provided with the respiration sensor 11, there is no need for the display control part 5 to include the respiration detection part 52 as shown in FIG. 17.

Second Embodiment

The second embodiment is explained below. The ensuing explanation will focus on the differences between the first and the second embodiments. Those components of the second embodiment which are substantially the same in structural terms as those discussed in connection with the first embodiment will be designated by the same reference numerals, and they will not be explained further in detail.

Figure 18:
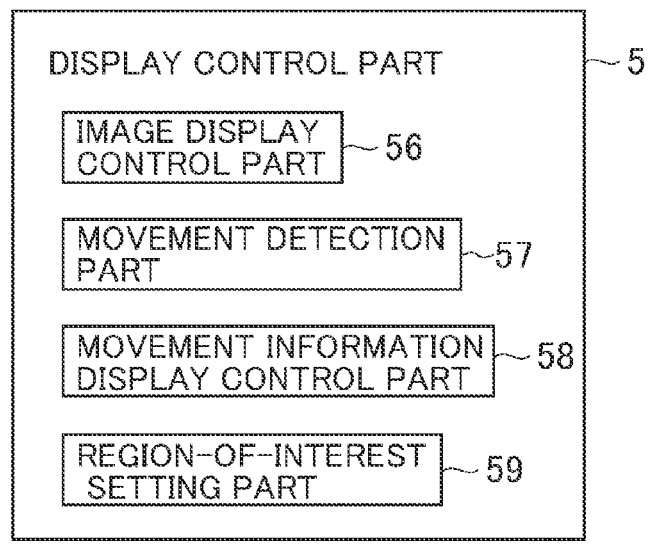
FIG. 18 is a block diagram showing a configuration of a display control part in a second embodiment.

The ultrasonic diagnosis apparatus of the second embodiment has the same configuration as that shown in FIG. 1. The echo data processing part 4 of the second embodiment has the same configuration as that shown in FIG. 2. In the second embodiment, the display control part 5 has an image display control part 56, a movement detection part 57, a movement information display control part 58, and a region-of-interest setting part 59 as shown in FIG. 18.

The image display control part 56 generates B-mode image data by scan-converting the B-mode data using a scan converter, and causes the display part 6 to display a B-mode image based on the generated B-mode image data. Also, the image display control part 56 generates elasticity image data by scan-converting the elasticity data using the scan converter, and causes the display part 6 to display an elasticity image based on the generated elasticity image data.

Figure 19:
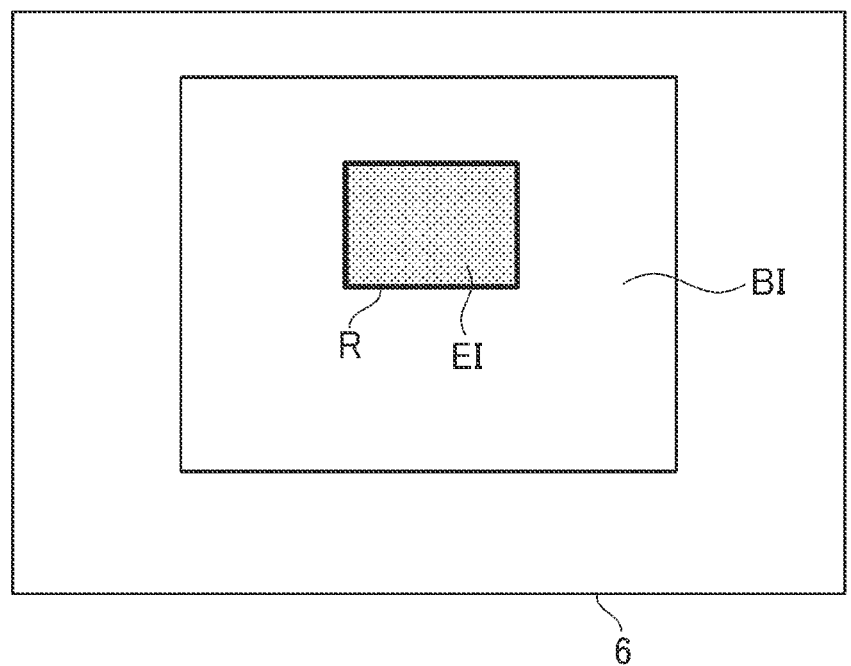
FIG. 19 is a diagram showing a display part displaying an elasticity image within the region of interest set in a B-mode image.

As shown in FIG. 19, the elasticity image EI is a two-dimensional image displayed within the region of interest R set in the B-mode image BI. The elasticity image EI is a color image having colors corresponding to the propagation velocity or elasticity coefficient mentioned above. The image display control part 56 merges the B-mode image data with the elasticity image data to generate composite image data, and causes the display part 6 to display an image based on the generated composite image data. Thus the elasticity image EI is a translucent image that lets the B-mode image IB appear in the background in translucent fashion.

The movement detection part 57 detects movements of the biological tissue in the test object (movement detection function). The movements of the test object's biological tissue include the movement of the biological tissue itself induced by heartbeats, respiration, or body motion, as well as changes in the position of the biological tissue relative to the ultrasonic probe 2 caused by changes in the position and angle of the probe 2 while the biological tissue remains still.

In the second embodiment, the movement detection part 57 detects the displacement of the biological tissue in the B-mode image through tracking by pattern matching using correlation calculations performed on the B-mode image data. More specifically, the movement detection part 57 performs correlation processing between the current and the preceding frames of B-mode image data to detect the displacement and the direction of the displacement in a two-dimensional direction (two-dimensional pattern matching). The correlation processing is a process that involves examining the correlation between two images, such as cross-correlation calculation. The movement detection function above is an example of the movement detection function.

The movement detection part 57 may detect the displacement of the biological tissue in the B-mode image through computing optical flow between two frames of B-mode image data (optical-flow technique). The variance of the vector angles from optical flow motion fields may be used to generate periodic curves related to the heart beating motion.

The method of detecting the displacement of the biological tissue by the movement detection part 57 is not limited to above methods.

The movement information display control part 58 causes the display part 6 to display a graph indicative of a chronological change in the displacement of the biological tissue detected by the movement detection part 57 (display control function). The operations involved will be discussed later in detail. The display control function above is an example of the notification function.

The region-of-interest setting part 59 sets a region of interest R in which the elasticity image IE is to be displayed. More specifically, the region-of-interest setting part 59 sets the region of interest R based on the input made by the operator through the operation part 7. The region of interest R is a region where shear waves are to be detected. It is in this region that the measuring ultrasonic pulses are transmitted and received.

Also in the second embodiment, the control part 8 executes the function of the transmit/receive beamformer 3 using the programs read from the storage part 9, thereby causing the ultrasonic probe 2 to transmit ultrasonic waves such as the push pulses and measuring ultrasonic pulses (transmission control function). This transmission control function is an example of the transmission control function.

The workings of the second embodiment are explained below. Unlike the first embodiment, the second embodiment has the elasticity image EI displayed inside the region of interest R set in the B-mode image BI. The workings will be explained more specifically with reference to the flowchart of FIG. 20.

First in step S11, the operator gets the ultrasonic probe 2 to transmit and receive B-mode imaging ultrasonic waves to and from, say, the liver. The image display control part 51 generates B-mode image data based on the echo signal obtained by the ultrasonic probe 2, and causes the display part 6 to display a B-mode image accordingly. The operator adjusts the position and angle of the ultrasonic probe 2 in such a manner that a B-mode image of the cross section desired to be observed will be displayed. When the desired cross section is displayed for observation, the operator secures the ultrasonic probe 2 in position and causes it to transmit and receive ultrasonic waves to and from the cross section in question. The operator may set the region of interest R in the B-mode image when this image is displayed in step S11.

Figure 21:
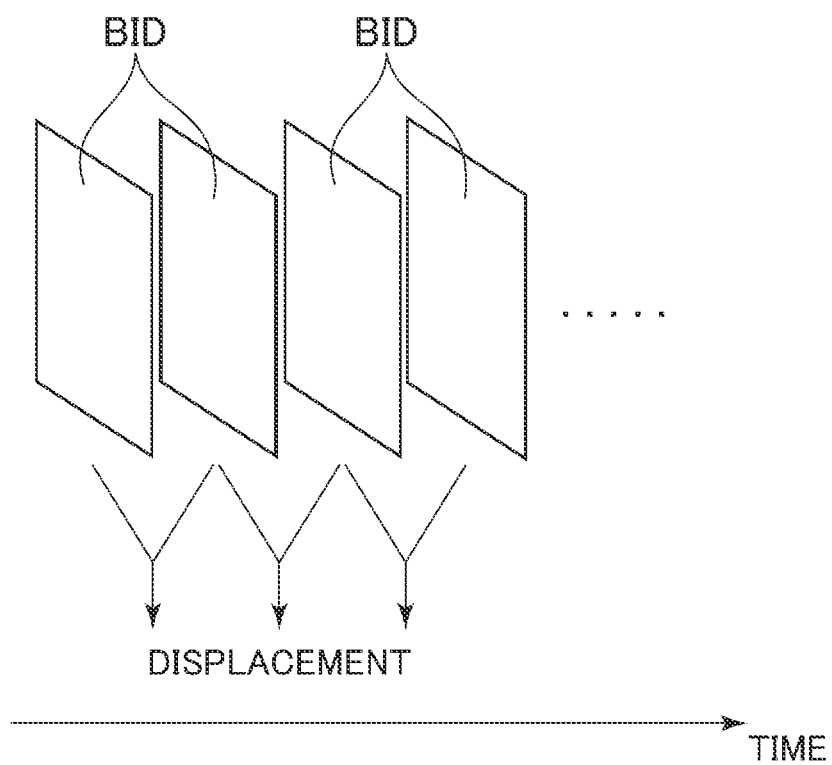
FIG. 21 is a diagram for explaining how displacements are detected.
Figure 22:
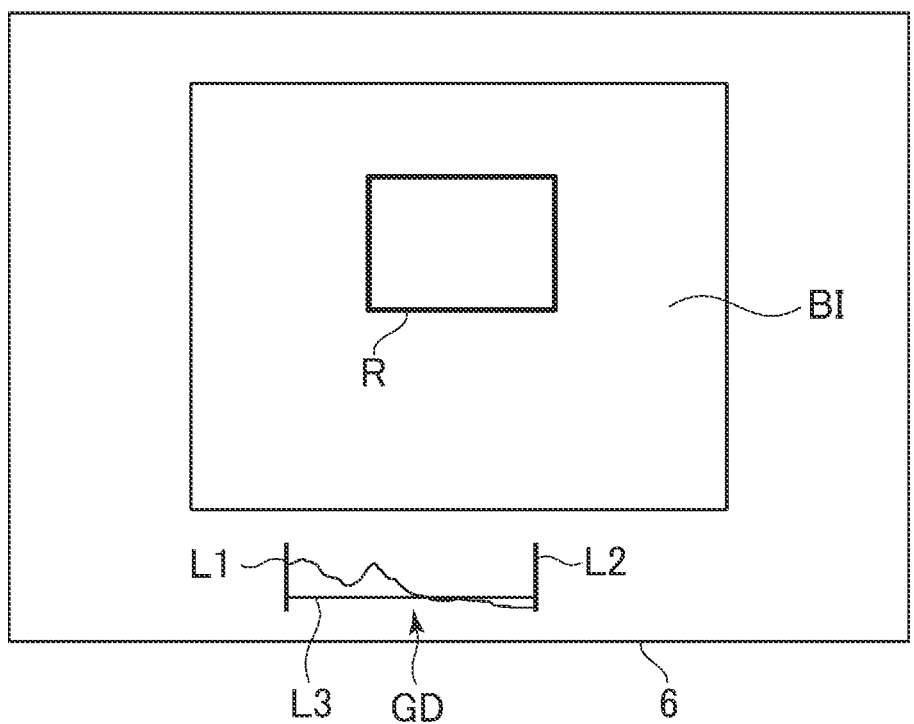
FIG. 22 is a diagram showing a display part displaying a graph indicative of a chronological change in displacement.

Also in step S11 above, the movement detection part 57 detects the displacement D of the biological tissue based on two frames of B-mode image data BID, as shown in FIG. 21. The movement information display control part 58 causes the display part 6 to display a graph GD indicative of a chronological change in the displacement D detected by the movement detection part 57, as indicated in FIG. 22.

The graph GD is displayed between lines L1 and L2 extending in the vertical direction. The horizontal axis of the graph GD represents time and its vertical axis denotes the displacement D. For example, the rightmost line L2 stands for the displacement D at the present moment. A line L3 extending in the horizontal direction represents a threshold value Dth of the displacement D. The threshold value Dth is explained below. The threshold value Dth is set to a value such that if the measuring ultrasonic pulses are transmitted and received to and from the biological tissue, as will be discussed later, with the displacement D of the tissue kept less than the threshold value Dth, the movement of the biological tissue will be minimal and an elasticity image with a good S/N ratio will be obtained.

If the movement detection part 57 performs tracking on a number of locations in each frame, then the displacement D of the biological tissue may be the sum of displacements of these multiple locations.

Next in step S12, the operator observing the graph GD determines whether the displacement D of the biological tissue is less than the threshold value Dth above. As long as the graph GD remains on or above the line L3 in the horizontal direction, the operator does not input any instruction ("No" in step S12) and continues to observe the graph GD.

On the other hand, if the graph GD appears below the horizontal line L3, the operator determines that the displacement D of the biological tissue is less than the threshold value Dth ("Yes" in step S12) and goes to step S13. In step S13, the operator inputs through the operation part 7 instructions to transmit push pulses and measuring ultrasonic pulses. That is, when the displacement D of the biological tissue becomes less than the threshold value Dth, it is time to transmit the push pulses and measuring ultrasonic pulses.

When the instructions are input in step S13 above, step S14 is reached. In step S14, the control part 8 executes the function of the transmit/receive beamformer 3 to transmit the push pulses and measuring ultrasonic pulses. More specifically, the transmit/receive beamformer 3 first causes the ultrasonic probe 2 to transmit the push pulses to the biological tissue. The transmit/receive beamformer 3 then causes the ultrasonic probe 2 to transmit the measuring ultrasonic pulses to the biological tissue. The measuring ultrasonic pulses are transmitted to detect shear waves in the biological tissue induced by the push pulses and measure the propagation velocity of the detected shear waves. The ultrasonic probe 2 then receives an echo signal of the measuring ultrasonic pulses.

The transmission and reception of the measuring ultrasonic pulses are carried out as many times as the number of sound rays in the region of interest R. Following a single push pulse transmission, the transmission and reception of the measuring ultrasonic pulses may be performed regarding only a part of the sound rays in the region of interest R. In this case, the push pulses are transmitted a number of times and the echo signal of the measuring ultrasonic pulses is obtained with regard to all sound rays in the region of interest R.

When the echo signal of the measuring ultrasonic pulses is obtained in step S14 above, step S15 is reached. In step S15, the propagation velocity calculation part 42 calculates the propagation velocity of the shear waves. The elasticity coefficient calculation part 43 calculates the elasticity coefficient (Young's modulus in pascals (Pa)) based on the propagation velocity thus calculated. Alternatively, only the propagation velocity may be calculated while the elasticity coefficient is omitted.

The image display control part 51 generates one frame of elasticity image data based on the propagation velocity data or the elasticity coefficient data described above. As shown in FIG. 19, the image display control part 51 causes the display part 6 to display within the region of interest R the elasticity image EI based on the elasticity image data. The storage part 9 may store image data resulting from the merging of one frame of the generated elasticity image data with the B-mode image data.

The image data above may be stored into the storage part 9 by the operator inputting a storage instruction through the operation part 9. Alternatively, without recourse to the input of the storage instruction, every time one frame of the elasticity image data is created, the data may be stored automatically into the storage part 9.

The storage part 9 may store data including the image resulting from the merging of the elasticity image data with the B-mode image data as well as data including the image of the graph GD. Furthermore, the storage part 9 may store data representing the value of the displacement D in effect when the instruction was input in step S13 above.

The elasticity image EI in one frame is obtained from the above-described processing. The operator may resume the transmission and reception of the B-mode imaging ultrasonic waves if wishing to obtain another elasticity image EI. Steps S11 through S15 above are then carried out.

According to the above-described second embodiment, the echo signal of the measuring ultrasonic pulses is obtained when the displacement D of the biological tissue is kept less than the threshold value Dth so that the movement of the biological tissue and that of the ultrasonic probe 2 are substantially inhibited. This makes it possible accurately to obtain values regarding the elasticity of the biological tissue such as propagation velocity and elasticity coefficient. Also, with the noise in the echo signal inhibited, the elasticity image EI with a good S/R ratio can be acquired.

Figure 23:
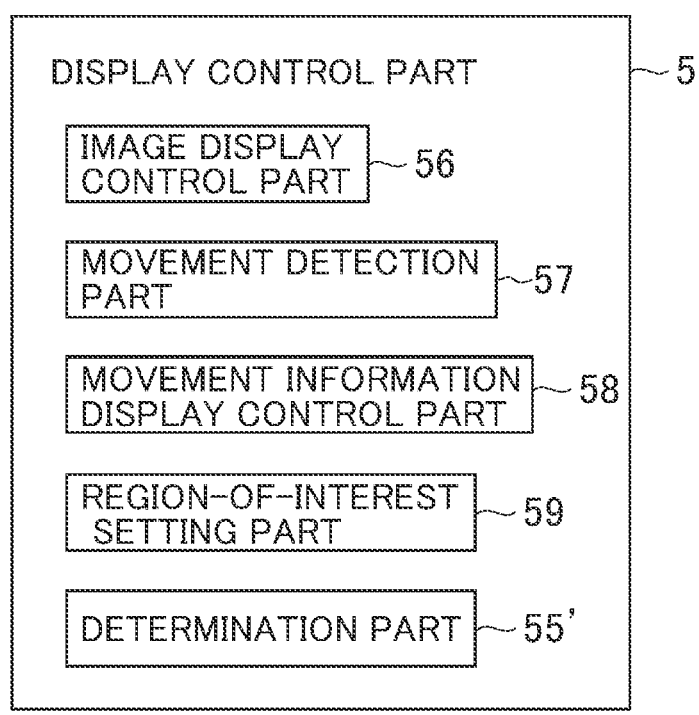
FIG. 23 is a block diagram showing a configuration of a display control part in a first variation of the second embodiment.

Some variations of the second embodiment will now be explained. A first variation is explained first. In the first variation, as shown in FIG. 23, the display control part 5 has a determination part 55'. This determination part 55' will be discussed later.

Figure 24:
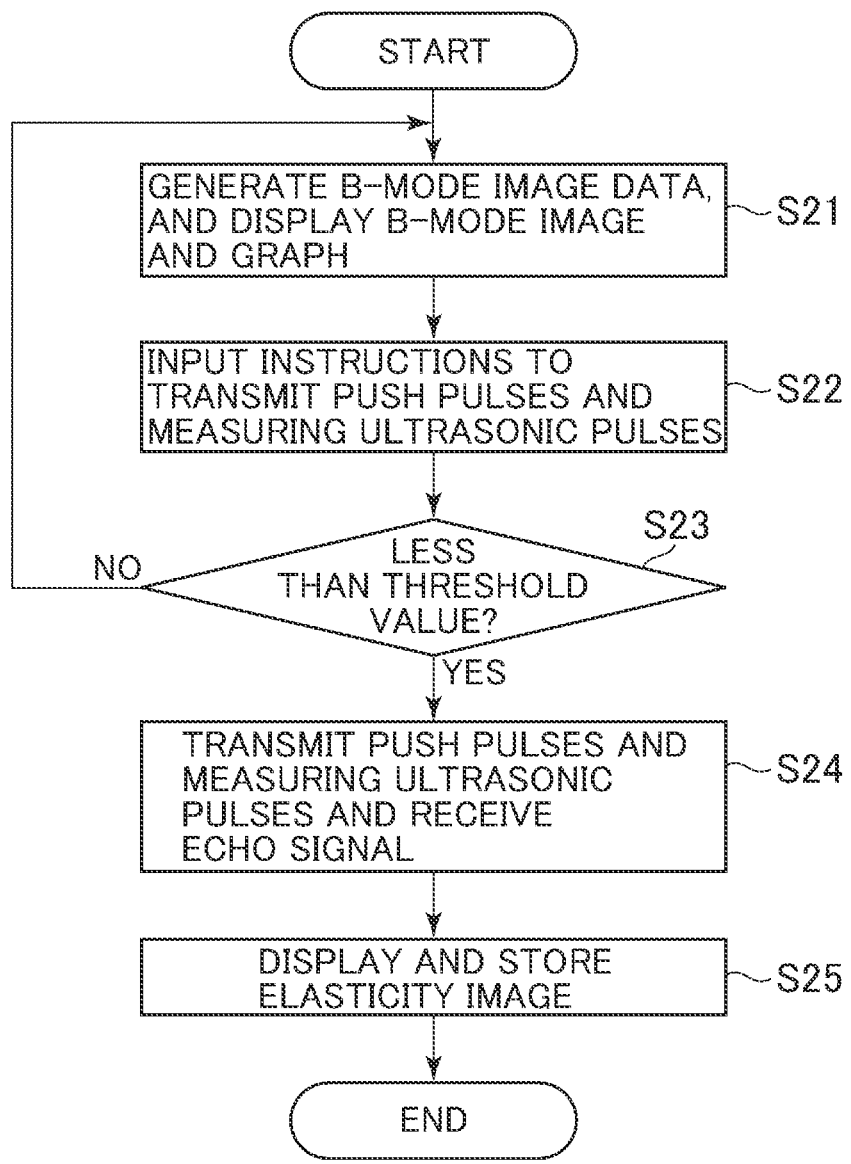
FIG. 24 is a flowchart showing a processing flow of the ultrasonic diagnosis apparatus in the first variation of the second embodiment.

The workings of the first variation of the second embodiment are explained below. When the instructions to transmit push pulses and measuring ultrasonic pulses are input through the operation part 9, the push pulses and measuring ultrasonic pulses are transmitted only if the displacement D of the biological tissue is less than the threshold value Dth. The operations involved will be described below in specific terms with reference to the flowchart of FIG. 24. In the flowchart of FIG. 24, steps S21, S24 and S25 represent the same processes as those of steps S11, S14 and S15 described above and thus will not be discussed further.

It should be noted that in step S21, the graph GD may not always be displayed.

In step S22, the operator inputs through the operation part 7 the instructions to transmit push pulses and measuring ultrasonic pulses. Next in step S23, the determination part 55' determines whether the displacement D of the biological tissue detected by the movement detection part 57 is less than the threshold value Dth. If the determination part 55' determines that the displacement D of the biological tissue is less than the threshold value Dth ("Yes" in step S23), control is passed to step S24. In step S24, the push pulses and measuring ultrasonic pulses are transmitted, and the echo signal of the measuring ultrasonic pulses is received. On the other hand, if the determination part 55' determines that the displacement D of the biological tissue is not less than the threshold value Dth ("No" in step S23), control is returned to step S21 and the B-mode imaging ultrasonic waves are transmitted and received.

According to the first variation of the second embodiment, when relevant instructions are input through the operation part 7, the push pulses and the measuring ultrasonic pulses are transmitted only if the determination part 55' determines that the displacement D of the biological tissue is less than the threshold value Dth. Because the instructions input through the operation part 7 become effective when the displacement D of the biological tissue is determined to be less than the threshold value Dth, the echo signal of the measuring ultrasonic pulses is obtained with the movement of the biological tissue and that of the ultrasonic probe 4 inhibited unfailingly.

Figure 25:
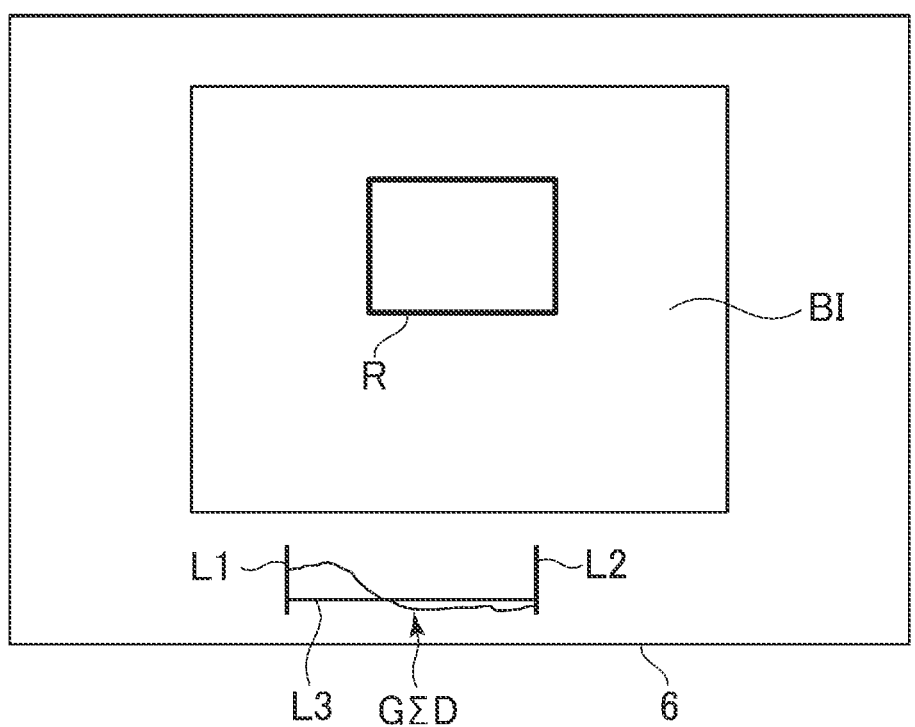
FIG. 25 is a diagram showing a display part displaying a graph indicative of a chronological change in the difference between pixel sums of B-mode image data in relation to a second variation of the second embodiment.

A second variation of the second embodiment is explained below. The processing of the second variation of the second embodiment is basically the same as the steps S11 through S15 and S21 through S25. However, with the second variation, the movement detection part 57 in steps S11 or S21 above calculates a sum Σ of the pixels in the B-mode image data in each frame in place of the displacement D of the biological tissue. Alternatively, the pixel sum Σ may be that of the B-mode data provided as raw data. The movement detection part 57 calculates a difference ΣD between the pixel sum Σ of the most recent (current) frame and that of the preceding frame. The difference ΣD is an absolute value. As shown in FIG. 25, the movement information display control part 58 causes the display part 6 to display a graph GΣD indicative of a chronological change in the difference ΣD.

When the biological tissue or the ultrasonic probe 2 moves, the value of the B-mode image data changes and so does the sum Σ above. It follows that the difference ΣD may be used to detect the movement of the biological tissue. Thus if the difference ΣD is determined to be less than a threshold value ΣDth in step S12 above, the operator inputs through the operation part 7 the instructions to transmit push pulses and measuring ultrasonic pulses in step S13 above. Also with the second variation, the determination part 55' in step S23 above determines whether the difference ΣD is less than the threshold value ΣDth. With this variation, the horizontal line L3 in the graph GΣD represents the threshold value ΣDth. When the difference ΣD is less than the threshold value ΣDth, the movement of the biological tissue is minimal, so that an elasticity image with a good S/N ratio can be obtained.

Also with the second variation, in step S15 the graph ΣGD is stored instead of the graph GD and the difference ΣD is stored in place of the displacement D.

Figure 26:
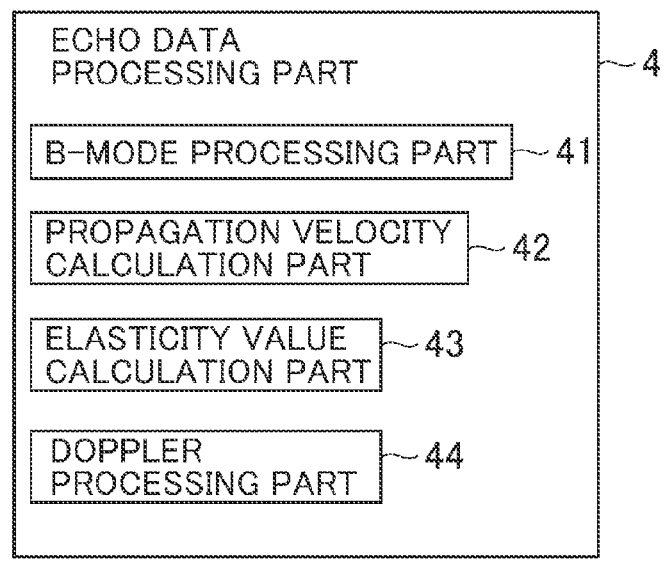
FIG. 26 is a block diagram showing a configuration of an echo data processing part in a third variation of the second embodiment.

A third variation of the second embodiment will now be explained. As shown in FIG. 26, the echo data processing part 4 of the third variation has a Doppler processing part 44 in addition to the above-described B-mode processing part 41, propagation velocity calculation part 42, and elasticity coefficient calculation part 43. The Doppler processing part 44 detects the moving velocity of the biological tissue by carrying out Doppler processing on the echo data obtained from the biological tissue (movement detection function). For example, the Doppler processing part 44 generates color Doppler data including velocity information by performing color Doppler processing to generate a color Doppler image. The Doppler processing part 44, it should be noted, may perform pulse Doppler processing to generate images by the pulse Doppler method or may carry out continuous wave Doppler processing to generate images by the continuous wave Doppler method. The movement detection function provided by the Doppler processing part 44 above is an example of the movement detection function.

Figure 27:
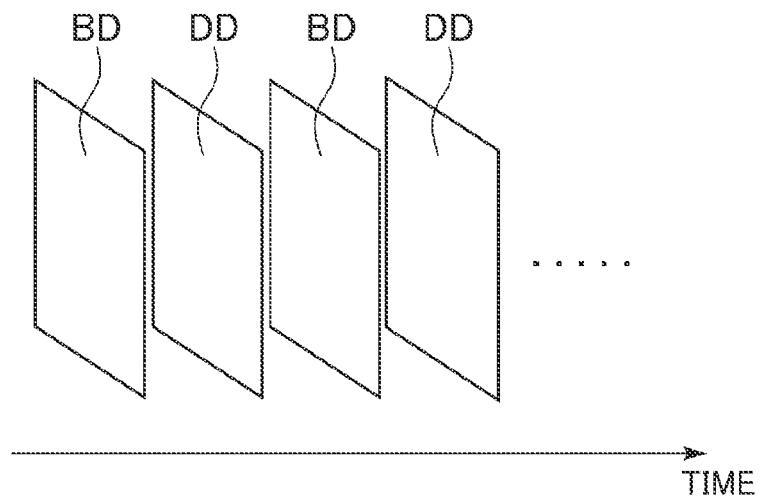
FIG. 27 is a diagram for explaining how moving velocity is detected.
Figure 28:
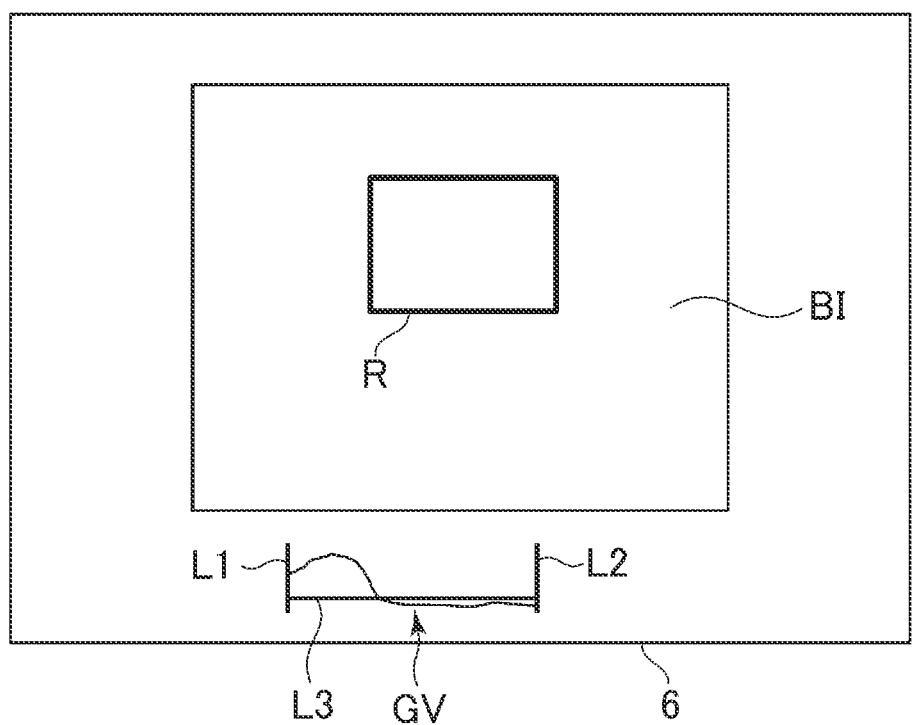
FIG. 28 is a diagram showing a display part displaying a graph indicative of a chronological change in velocity.

The processing of the third variation of the second embodiment is basically the same as the steps S11 through S15 and S21 through S25. However, with the third variation, in step S11 or S21 above, the transmission and reception of B-mode imaging ultrasonic waves and the transmission and reception of Doppler ultrasonic waves are performed alternately, frame by frame, to generate B-mode data BD and color Doppler data DD alternately as shown in FIG. 27. On the basis of the data about the velocity V in the color Doppler data DD, the movement information display control part 58 causes the display part 6 to display a graph GV indicative of a chronological change in the velocity G as shown in FIG. 28.

When the biological tissue or the ultrasonic probe 2 moves, the data about the velocity V is obtained from the color Doppler data. Thus if the operator determines in step S12 above that the velocity V is less than a threshold value Vth in the graph GV, step S13 is reached and the operator inputs through the operation part 7 the instructions to transmit push pulses and measuring ultrasonic pulses. The determination part 55' determines in step S23 above whether the velocity V is less than the threshold value Vth. In this example, the horizontal line L3 in the graph GV represents the threshold value Vth. If the velocity V is less than the threshold value Vth, the movement of the biological tissue is minimal, so that an elasticity image with a good S/N ratio can be obtained.

Also with the third variation, in step S15 above the graph GV is stored instead of the graph GD and the velocity V is stored in place of the displacement D.

Figure 29:
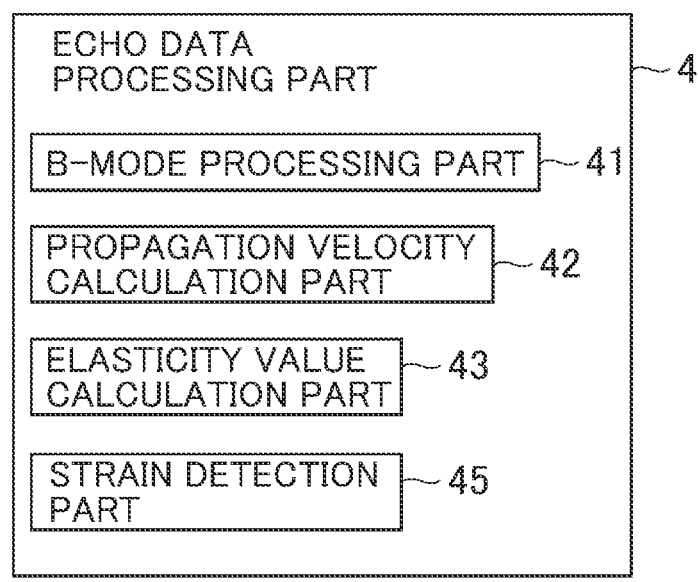
FIG. 29 is a diagram showing a configuration of an echo data processing part in a fourth variation of the second embodiment.

A fourth variation of the second embodiment will now be explained. As shown in FIG. 29, the echo data processing part 4 of the fourth variation has a strain detection part 45 in addition to the above-described B-mode processing part 41, propagation velocity calculation part 42, and elasticity coefficient calculation part 43. The strain detection part 45 detects strains in various locations of the biological tissue based on the echo data that is obtained from the biological tissue and output from the transmit/receive beamformer 3 (movement detection function). The strain detection part 45 sets correlation windows in chronologically different echo data along the same sound ray over a single scanning plane (i.e., different frames of echo data), and generates strain data by detecting strains through correlation calculations performed between the correlation windows, as described in Japanese Unexamined Patent Publication No. 2008-126079, for example. The movement detection function provided by the strain detection part 45 is an example of the movement detection function.

Figure 30:
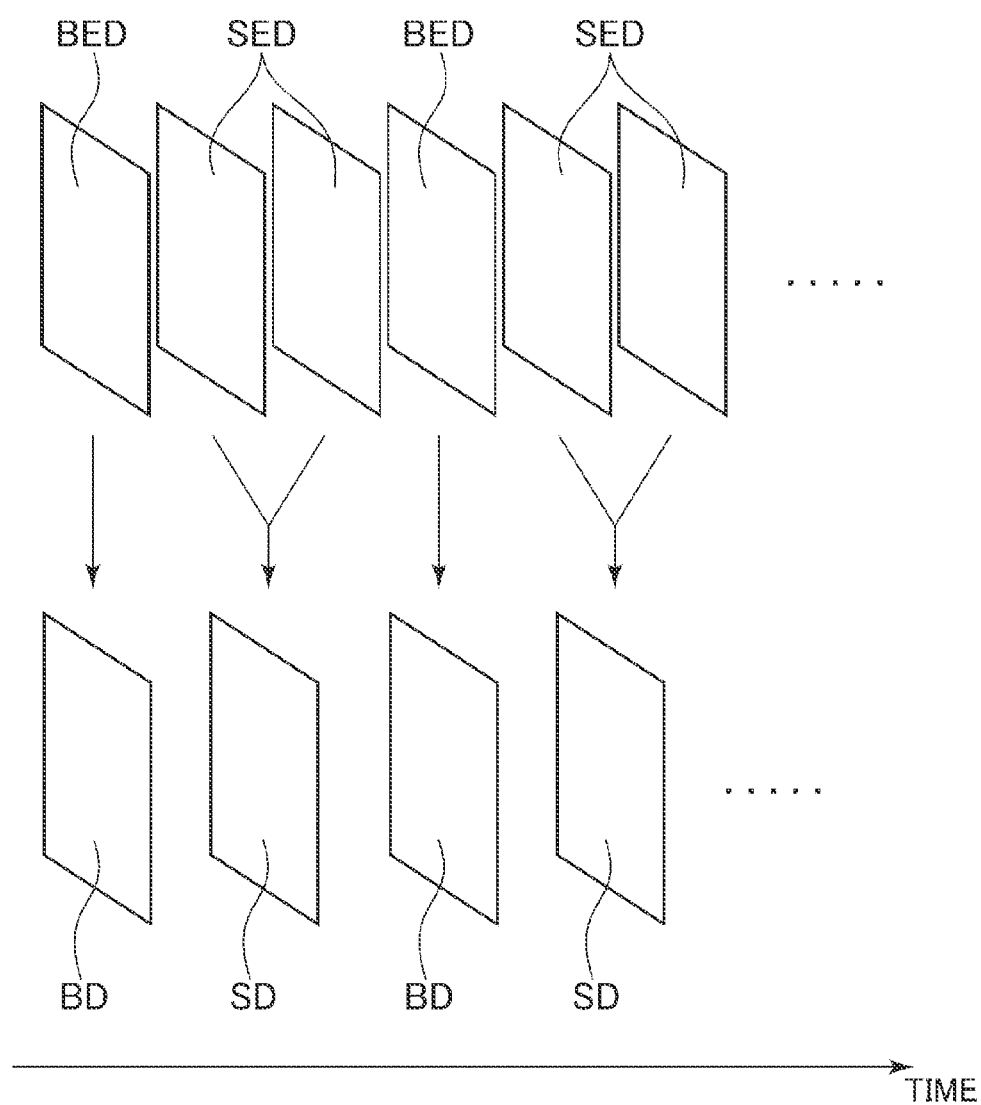
FIG. 30 is a diagram for explaining how strain is detected.

With this variation, in step S11 or S21 above, the B-mode imaging ultrasonic waves for one frame are transmitted and received, before the ultrasonic waves for two frames are transmitted and received for strain data generation, as shown in FIG. 30. In this manner, the B-mode echo data BED in one frame and the strain detection echo data SED in two frames are generated repeatedly.

Figure 31:
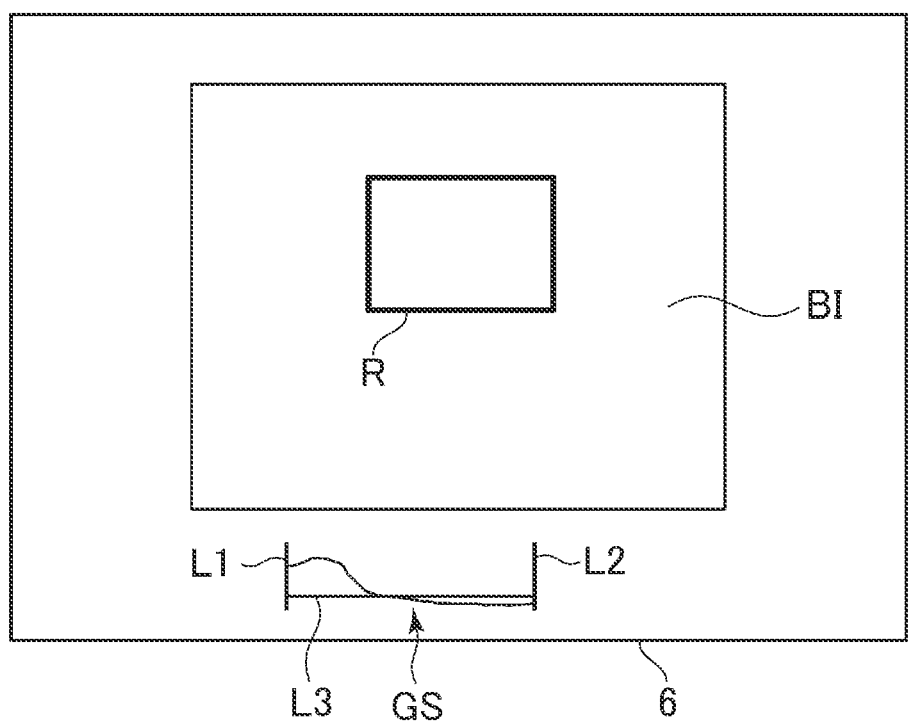
FIG. 31 is a diagram showing a display part displaying a graph indicative of a chronological change in strain.

The B-mode processing part 41 generates B-mode data BD based on the echo data BED above. Also, the strain detection part 45 calculates strain data SD on the basis of the echo data SED in two frames. The movement information display control part 58 causes the display part 6 to display a graph GS indicative of a chronological change in the value S represented by the strain data SD above, as shown in FIG. 31.

The biological tissue can be strained due to heartbeats and respiration. Thus if the operator determines in step S12 above that the strain S is less than a threshold value Sth, step S13 is reached and the operator inputs through the operation part 7 the instructions to transmit push pulses and measuring ultrasonic pulses. The determination part 55' determines in step S23 above whether the strain S is less than the threshold value Sth. In this example, the horizontal line L3 in the graph GS represents the threshold value Sth. If the strain S is less than the threshold value Sth, the movement of the biological tissue is minimal, so that an elasticity image with a good S/N ratio can be obtained.

Figure 32:
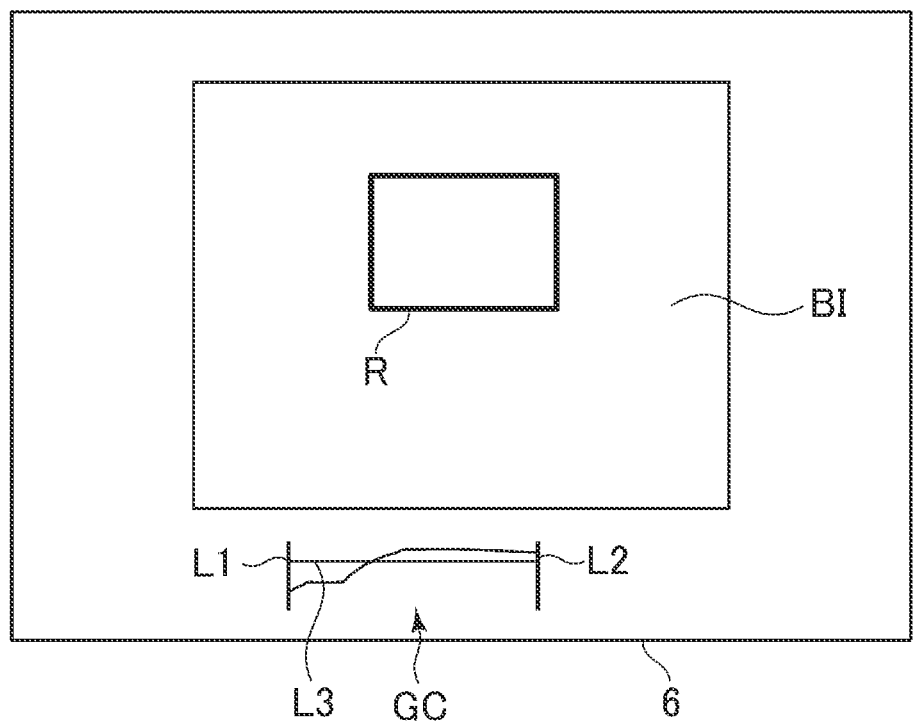
FIG. 32 is a diagram showing a display part displaying a graph indicative of a chronological change in a correlation coefficient.

In the fourth variation of the second embodiment, the movement information display control part 58 may cause the display part 6 to display, in place of the graph GS above, a graph GC indicative of a chronological change in the correlation coefficient C obtained through the correlation calculations performed by the strain detection part 45, as shown in FIG. 32.

Figure 20:
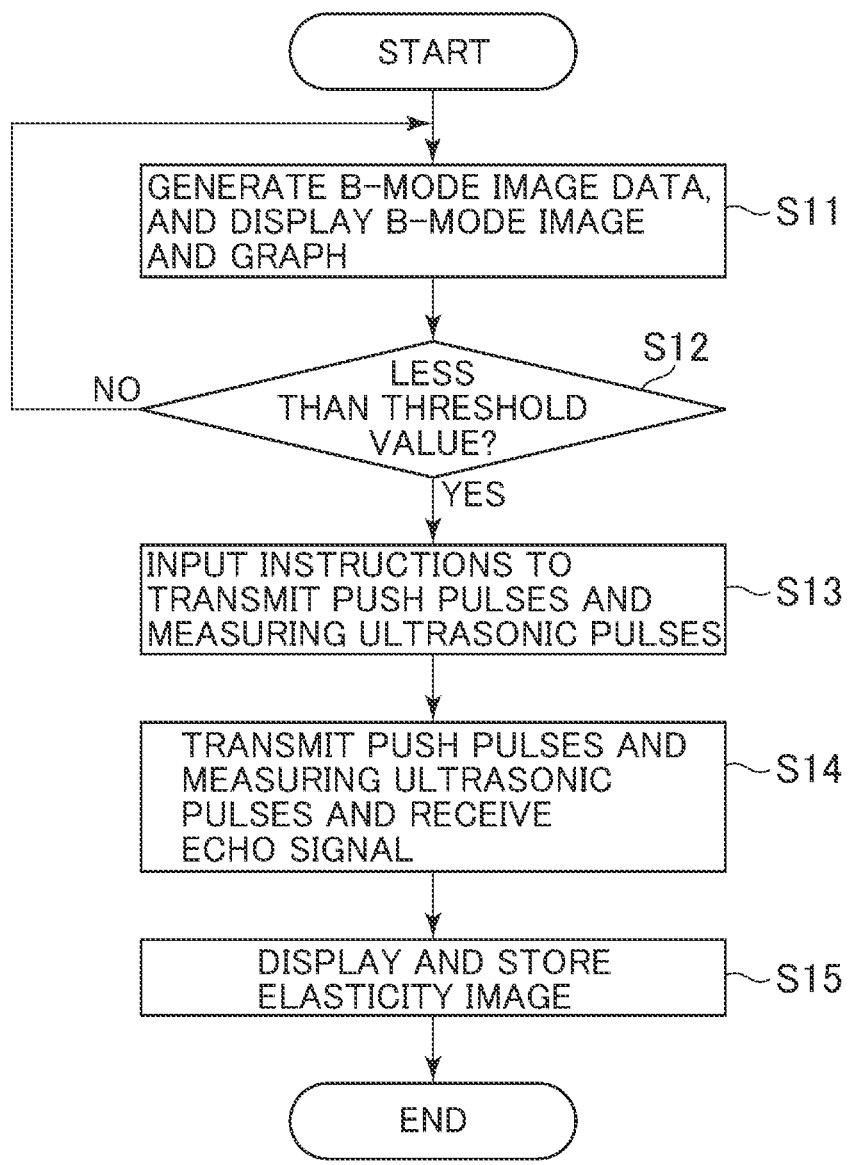
FIG. 20 is a flowchart showing a processing flow of the ultrasonic diagnosis apparatus in the second embodiment.
Figure 33:
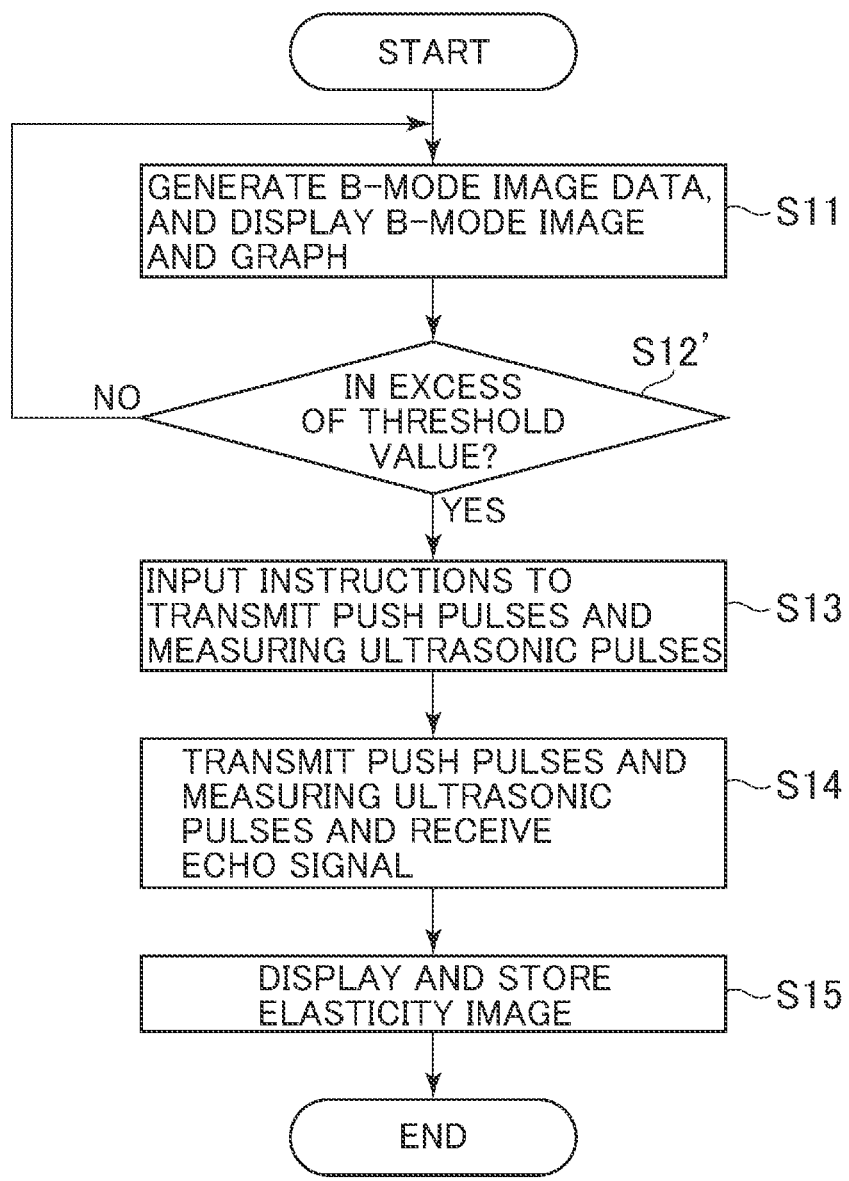
FIG. 33 is a flowchart showing another typical processing flow of the ultrasonic diagnosis apparatus in the fourth variation of the second embodiment.

The correlation coefficient C is set to be 0≤C≤1. The higher the correlation between two frames of the echo data SED, the larger the correlation coefficient C becomes; the lower the correlation, the smaller the coefficient. When the biological tissue or the ultrasonic probe 2 moves, the correlation between two frames of the echo data SED drops, so that the correlation coefficient C becomes smaller. It follows that the movement of the biological tissue can be detected using the correlation coefficient C.

Where the graph GC above is displayed, the flowchart of FIG. 33 applies in place of the flowchart of FIG. 20. The flowchart of FIG. 33 is the same as that of FIG. 20 except for step S12'. In step S12', the operator determines whether the correlation coefficient C in the graph GC exceeds a threshold value Cth. If the correlation coefficient C is determined to exceed the threshold value Cth, the operator in step S13 inputs through the operation part 7 the instructions to transmit push pulses and measuring ultrasonic pulses. In this example, the horizontal line L3 in the graph GC above represents the threshold value Cth. When the correlation coefficient C is in excess of the threshold value Cth, the movement of the biological tissue is minimal, so that an elasticity image with a good S/N can be obtained.

Figure 34:
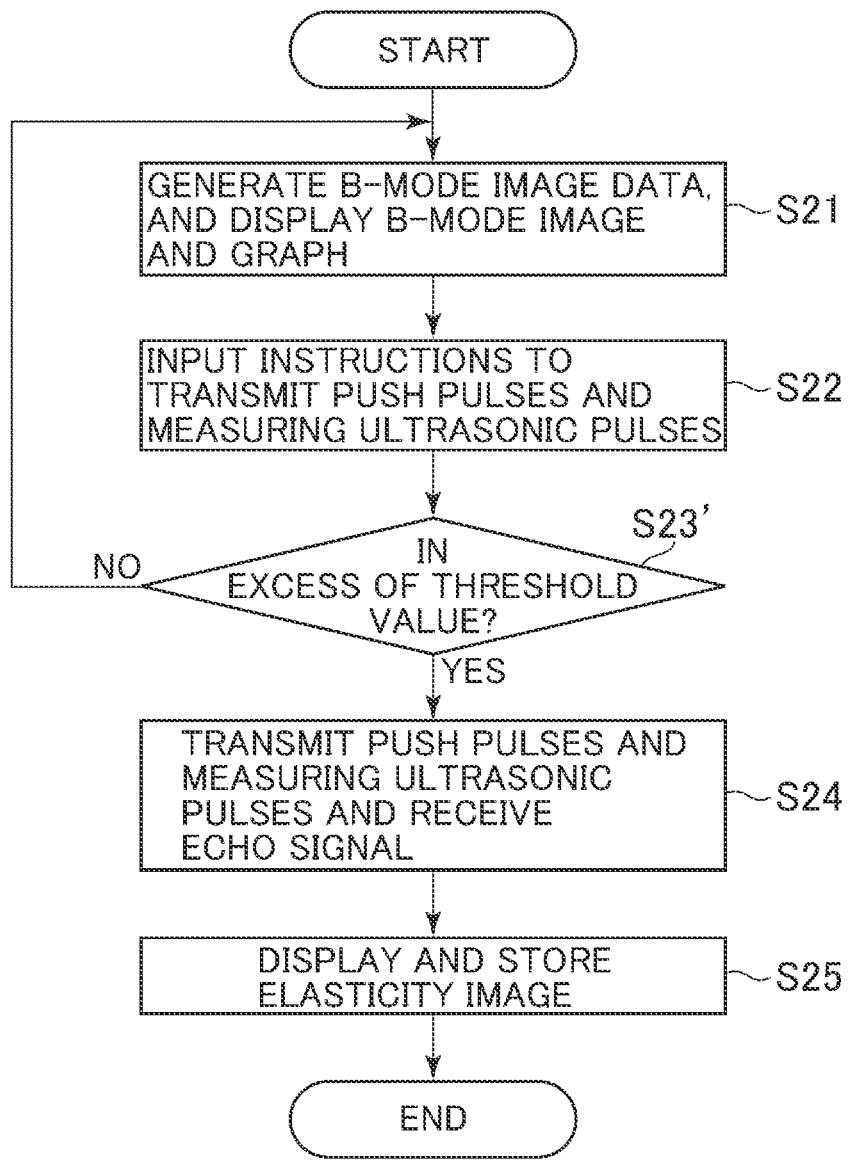
FIG. 34 is a flowchart showing another typical processing flow of the ultrasonic diagnosis apparatus in the fourth variation of the second embodiment.

Also, when the graph GC is displayed, the flowchart of FIG. 34 applies in place of the flowchart of FIG. 24. The flowchart of FIG. 34 is the same as that of FIG. 24 except for step S23'. In step S23', the determination part 55' determines whether the correlation coefficient C exceeds the threshold value Cth. If the determination part 55' determines that the correlation coefficient C is in excess of the threshold value Cth, control is passed to step S24.

Also with this variation, in step S15 above the graph GC is stored in place of the graph GD and the correlation coefficient C is stored instead of the displacement D.

Third Embodiment

The third embodiment is explained below. The ensuing explanation will focus on the differences between the third embodiment on the one hand and the first and the second embodiments on the other hand. Those components of the third embodiment which are substantially the same in structural terms as those discussed in connection with the first and the second embodiments will be designated by the same reference numerals, and they will not be explained further in detail.

The ultrasonic diagnosis apparatus of the third embodiment has the same configuration as that shown in FIG. 1. The echo data processing part 4 of the third embodiment has the same configuration as that shown in FIG. 2. The display control part 5 of the third embodiment has the same configuration as that shown in FIG. 23.

The workings of the third embodiment are explained below. As with the second embodiment, the elasticity image EI is displayed within the region of interest R. The operations involved will be explained hereunder in specific terms with reference to the flowchart of FIG. 35.

First in step S31, as in step S11 above, the operator causes the display part 6 to display a B-mode image and sets the region of interest R therein. The movement detection part 57 detects the movement of the biological tissue. For example, as with the second embodiment, the movement detection part 57 performs tracking on B-mode image data to detect the displacement D of the biological tissue D.

In this example, the graphic GD may or may not be displayed in step S31.

Next in step S32, the determination part 55' determines whether the displacement D of the biological tissue detected by the movement detection part 57 is less than the threshold value Dth. If the determination part 55' determines in step S32 above that the displacement D of the biological tissue is less than the threshold value Dth ("Yes" in step S32), control is passed to step S33. In step S33, the control part 8 causes the transmit/receive beamformer 3 to function to transmit push pulses and measuring ultrasonic waves. This operation causes the push pulses and measuring ultrasonic pulses to be transmitted and the echo signal of the measuring ultrasonic pulses to be received. On the other hand, if the determination part 55' determines that the displacement D of the biological tissue is not less than the threshold value Dth ("No" in step S32), then control is returned to step S31 and the B-mode imaging ultrasonic waves are transmitted and received.

In step S32 above, it may be arranged that control is passed to step S33 only if the determination that the displacement D is less than the threshold value Dth is performed a predetermined number of times consecutively.

Next in step S34, as in step S15 above, one frame of elasticity image data is generated and an elasticity image EI is displayed on the display part 6. And as in step S15 above, the storage part 9 may store the image data obtained by merging one frame of the generated elasticity image data with the B-mode image data. The storage part 9 may further store the graph GD and the displacement D in effect when the displacement D is determined to be less than the threshold value Dth so that the control part 8 causes the transmit/receive beamformer 3 to function.

Figure 36:
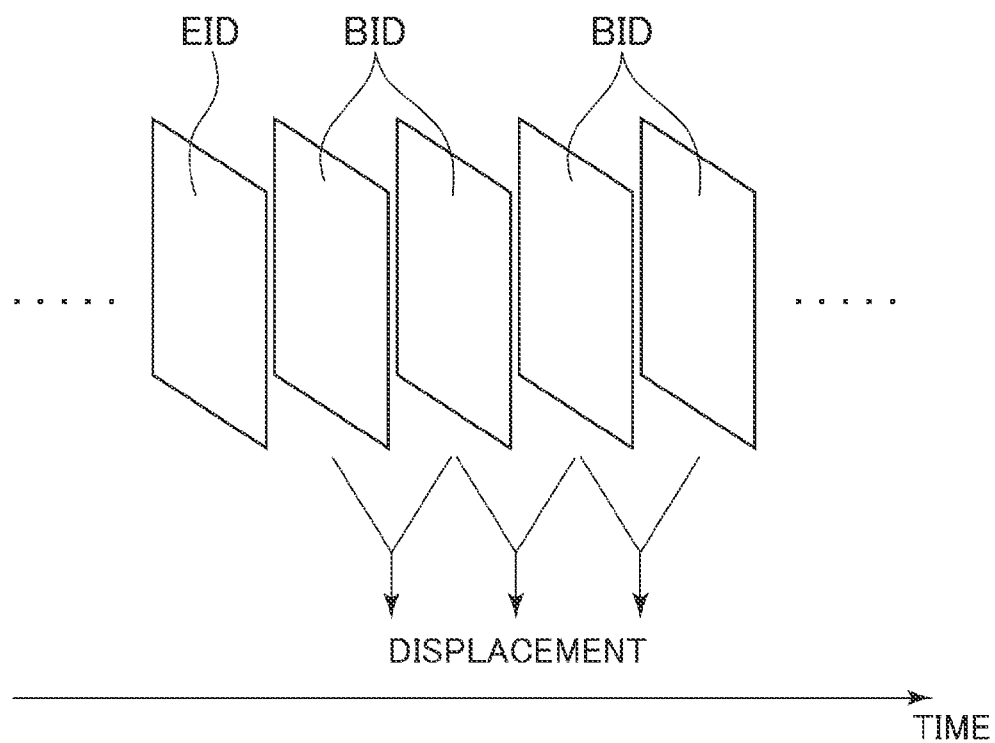
FIG. 36 is a diagram for explaining how displacements are detected after elasticity image data is generated.

Next in step S35, the control part 8 determines whether the elasticity image data is generated for the Nth time. The number N may be determined by the operator 7 manipulating the operation part 7. If it is determined that the elasticity image data is not generated for the Nth time ("No" in step S35), control is returned to step S31. In step S31, the B-mode imaging ultrasonic waves are again transmitted and received so that the displacement D of the biological tissue is detected based on two frames of the B-mode image data BID as shown in FIG. 36. In FIG. 36, reference character EID denotes the most recently generated elasticity image data.

On the other hand, if it is determined that the elasticity image data is generated for the Nth time ("Yes" in step S35), then the process is terminated. In this manner, the elasticity image in N frames is generated.

In the third embodiment, the push pulses and the measuring ultrasonic pulses are transmitted when the determination part 55' determines that the displacement D is less than the threshold value Dth. Thus while the movement of the biological tissue and that of the ultrasonic probe 2 are being inhibited as in the case of the second embodiment, the echo signal of the measuring ultrasonic pulses is obtained. In this manner, the third embodiment provides the same advantages as the second embodiment.

The movement of the biological tissue induced by heartbeats or respiration is periodic. Thus the determination part 55' may detect a cycle T of the time point at which the displacement D is less than the threshold value Dth. In this case, the push pulses and the measuring ultrasonic pulses are transmitted in the cycle T by the instruction of the control part 8.

There may be such a case that the echo signal of the measuring ultrasonic pulses with regard to all sound rays in the region of interest R isn't obtained in the period in which the displacement D is less than the threshold value Dth. In this case, the transmission of the push pulses, and the transmission and reception of the measuring ultrasonic pulses are carried out every cycle T until the echo signal of the measuring ultrasonic pulses is obtained with regard to all sound rays in the region of interest R. The elasticity image data in one frame is generated based on echo signals of the measuring ultrasonic pulses which are obtained a number of times.

With the third embodiment, as with the second variation of the second embodiment, the difference ΣD between the pixel sum Σ of the most recent (current) frame and that of the preceding frame nay be calculated in place of the displacement D of the biological tissue. In this case, the determination part 55' determines in step S32 above whether the difference ΣD is less than the threshold value ΣDth. If the difference ΣD is determined to be not less than the threshold value ΣDth, control is passed to step S33 above; if the difference ΣD is determined to be less than the threshold value ΣDth, control is returned to step S31 above.

Alternatively, as with the third variation of the second embodiment, the echo data processing part 4 may have the configuration shown in FIG. 26. The velocity V may be calculated by the Doppler processing part 44 in place of the displacement D of the biological tissue. In this case, the determination part 55' determines in step S32 above whether the velocity V is less than the threshold value Vth. If the velocity V is determined to be not less than the threshold value Vth, control is passed to step S33 above; if the velocity V is determined to be less than the threshold value Vth, control is returned to step S31 above.

Alternatively, as with the fourth variation of the second embodiment, the echo data processing part 4 may have the configuration shown in FIG. 29. The strain S may be detected by the strain detection part 45 in place of the displacement D of the biological tissue. In this case, the determination part 55' determines in step S32 above whether the strain S is less than the threshold value Sth. If the strain S is determined to be not less than the threshold value Sth, control is passed to step S33 above; if the strain S is determined to be less than the threshold value Sth, control is returned to step S31 above.

Figure 37:
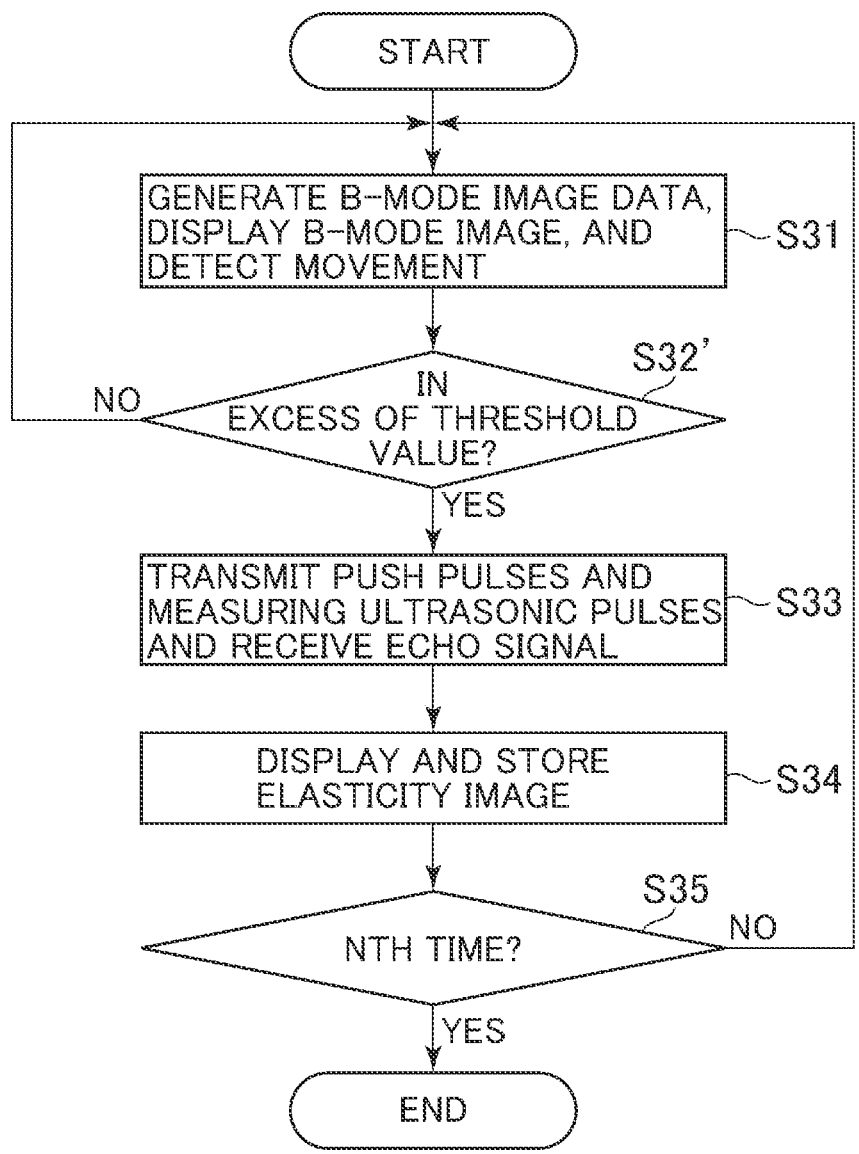
FIG. 37 is a flowchart showing another typical processing flow of the ultrasonic diagnosis apparatus in the third embodiment.

As another alternative, the determination part 55' may perform the determination using not the strain S but the correlation coefficient C obtained through the correlation calculations carried out on the strain S. Specifically, as shown in the flowchart of FIG. 37, the determination part 55' determines in step S32' whether the correlation coefficient C exceeds the threshold value Cth. If the correlation coefficient C is determined to exceed the threshold value Cth, control is passed to step S33 above; if the correlation coefficient C is determined to be not in excess of the threshold value Cth, control is returned to step S31 above. It should be noted that the steps in the flowchart of FIG. 37 are the same as those in FIG. 35 except for step S32' above.

Fourth Embodiment

The fourth embodiment is explained below. The ensuing explanation will focus on the differences between the fourth embodiment on the one hand and the first, the second, and the third embodiments on the other hand. Those components of the fourth embodiment which are substantially the same in structural terms as those discussed in connection with the first, the second, and the third embodiments will be designated by the same reference numerals, and they will not be explained further in detail.

The ultrasonic diagnosis apparatus of the fourth embodiment has the same configuration as that shown in FIG. 1. The echo data processing part 4 of the fourth embodiment has the same configuration as that shown in FIG. 2. The display control part 5 of the fourth embodiment has the same configuration as that shown in FIG. 23.

Figure 38:
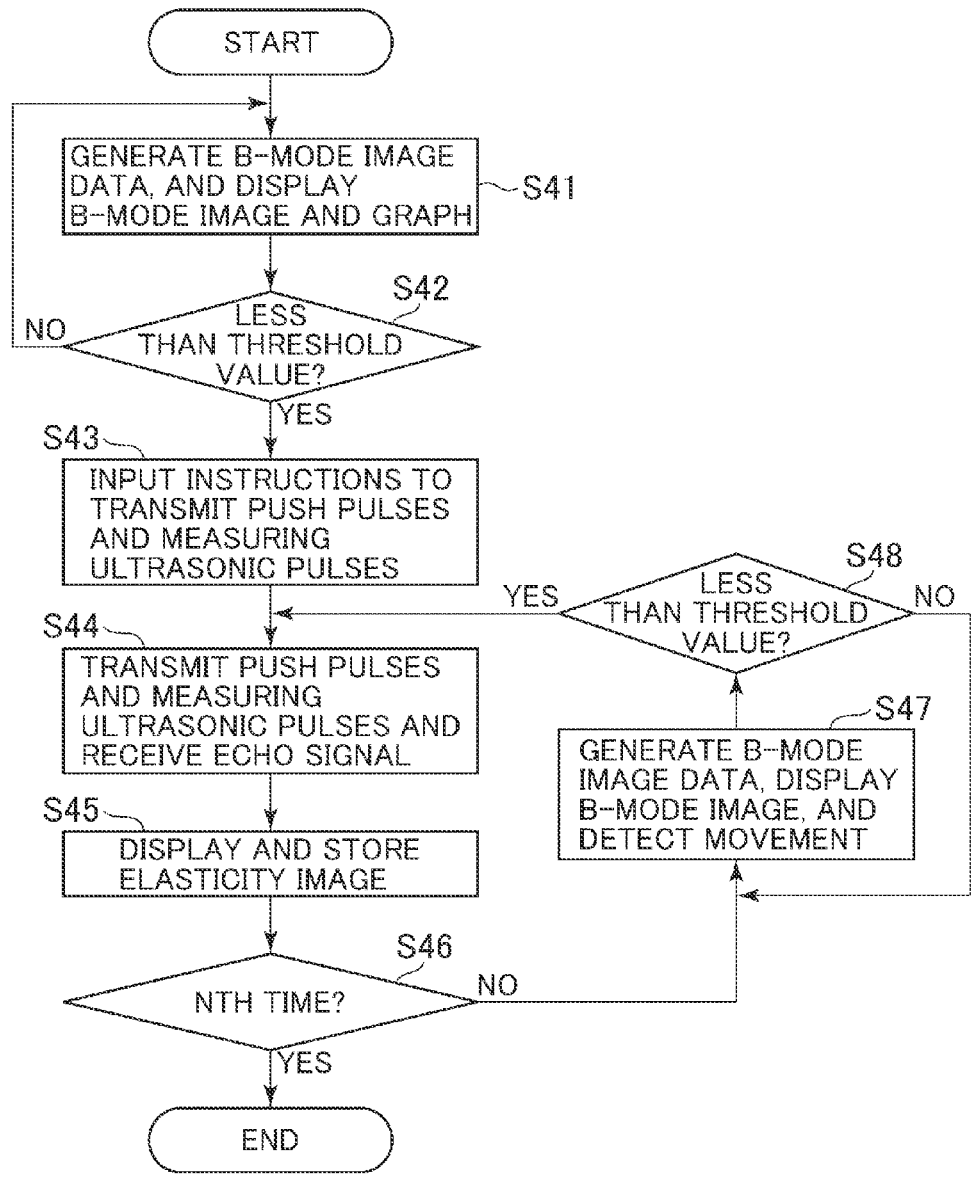
FIG. 38 is a flowchart showing a processing flow of an ultrasonic diagnosis apparatus in a fourth embodiment.

The workings of the fourth embodiment are explained below. In this example, the operator inputs through the operation part 7 the instructions to transmit the push pulses and measuring ultrasonic pulses, before an elasticity image in a number of frames is generated. The workings involved will be explained hereunder in specific terms with reference to the flowchart of FIG. 38.

The processes of steps S41 through S45 are the same as those of steps S11 through S15 above in the flowchart of FIG. 20. When steps S41 through S45 are carried out, if the displacement D is determined to be less than the threshold value Dth, the operator inputs the instructions to transmit the push pulses and measuring ultrasonic pulses, whereby the elasticity image data in one frame is generated.

In step S46, as in step S35 above, it is determined whether the elasticity image data is generated for the Nth time. It is assumed that N≥2 in this example. If it is determined that the elasticity image data is not generated for the Nth time ("No" in step S46), control is passed to step S47; if the elasticity image data is determined to be generated for the Nth time ("Yes" in step S46), the process is terminated.

In step S47, as in step S41 above, the B-mode imaging ultrasonic waves are again transmitted and received, and the displacement D of the biological tissue is detected based on two frames of B-mode image data BID. Furthermore, a B-mode image is displayed on the display part 6. However, unlike in step S41 above, the graph GD may or may not be displayed in step S47.

Figure 35:
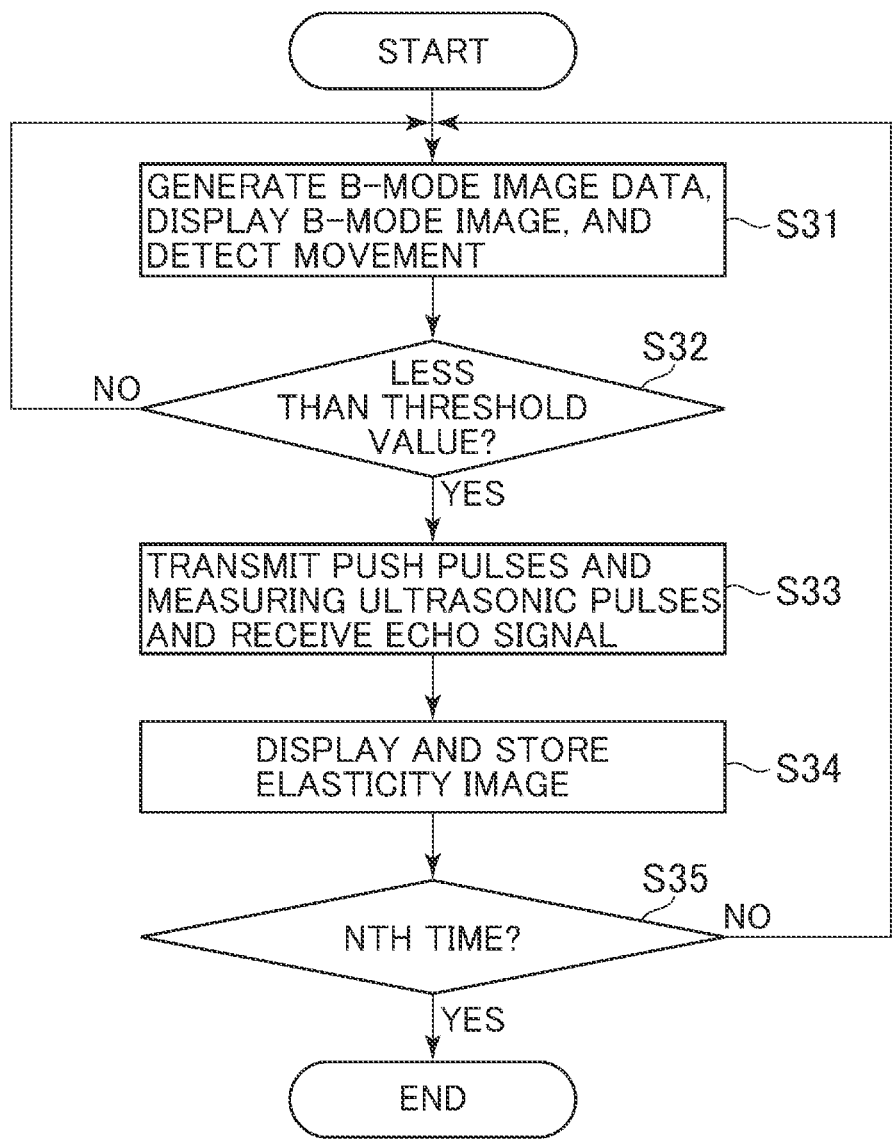
FIG. 35 is a flowchart showing a processing flow of an ultrasonic diagnosis apparatus in a third embodiment.

Next in step S48, as in step S32 above in the flowchart of FIG. 35, the determination part 55' determines whether the displacement D of the biological tissue detected by the movement detection part 57 is less than the threshold value Dth. If the determination part 55' determines that the displacement D of the biological tissue is less than the threshold value Dth ("Yes" in step S48), control is returned to step S44. The control part 8 then causes the transmit/receive beamformer 3 to function to transmit push pulses and measuring ultrasonic pulses.

On the other hand, if the determination part 55' determines that the displacement D of the biological tissue is not less than the threshold value Dth ("No" in step S48), control is returned to step S47, and the B-mode imaging ultrasonic waves are transmitted and received.

Also with the fourth embodiment, control may be passed from step S48 above to step S44 above only if the determination that the displacement D is less than the threshold value Dth is performed a predetermined number of times in a row.

According to the fourth embodiment, where a number of frames of elasticity image data are to be obtained, the echo signal of the measuring ultrasonic pulses can be acquired by the operator inputting the relevant instructions only once in step S43 above while the movement of the biological tissue and that of the ultrasonic probe 2 are being inhibited. The fourth embodiment thus provides the same advantages as the second and the third embodiments.

The fourth embodiment, as with the second and the third embodiments, may also utilize the above-described difference $\Sigma D$, velocity V, strain S, or correlation coefficient C in place of the displacement D of the biological tissue.

It should be understood that the disclosure is not limited to the above-described embodiments and their variations and that various changes, modifications and alternatives may so far as they are within the spirit and scope thereof. For example, the elasticity coefficient calculation part 43 may calculate as measurements of elasticity the displacement of the biological tissue induced by the push pulses transmitted to that tissue. In this case, the displacement is calculated on the basis of the echo signal of the measuring ultrasonic pulses transmitted to the biological tissue.

Whereas the above-described first embodiment calculates the average of elasticity coefficients and/or of propagation velocities as the result of a number of elasticity measurements that have been made, the result of multiple elasticity measurements is not limited to averages. Alternatively, the result of such multiple elasticity measurements may be a median value or an intermediate value between the maximum and the minimum elasticity coefficients obtained from these measurements.

Whereas the above-described first embodiment presents the waveform W as the image indicative of the secular change in respiration, this does not limit the systems and methods described herein. Alternatively, the image showing the secular change in respiration may be a bar graph, not shown, of which the height is varied with the respiration-induced up-down movement of the biological tissue. Furthermore, the images based on the evaluation of the respiration information are not limited to those provided by the embodiments discussed above.

Also, the first embodiment, as with the second through the fourth embodiments, may use two-dimensional regions as the target to be measured for elasticity.

Figure 39:
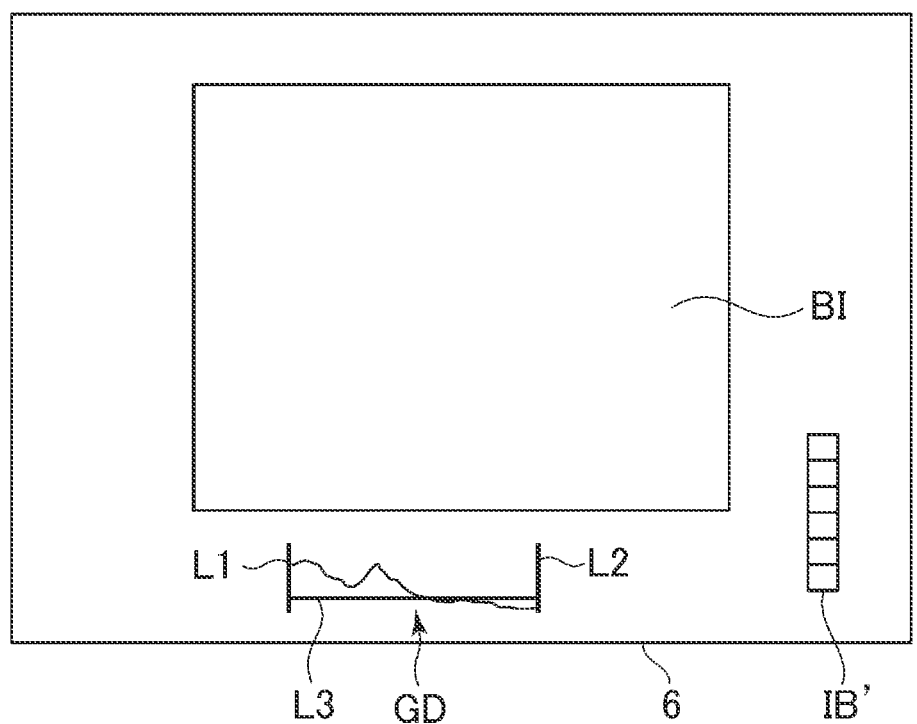
FIG. 39 is a diagram showing an indicator bar as another typical image indicative of a chronological change in the movement of a biological tissue.
Figure 40:
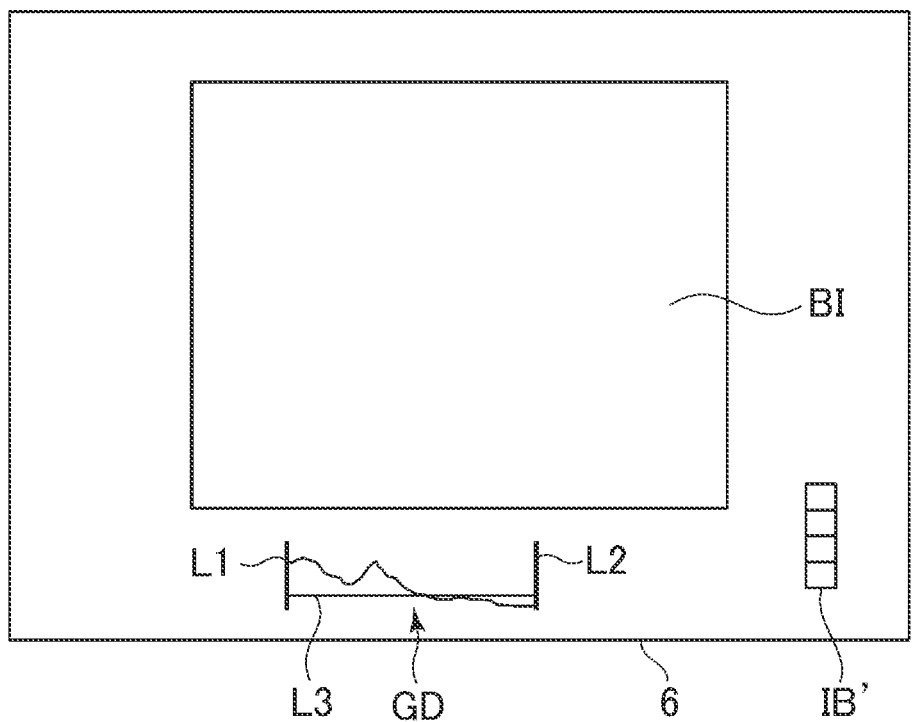
FIG. 40 is a diagram showing an indicator bar as another typical image indicative of a chronological change in the movement of a biological tissue.

With the second through the fourth embodiments, the image indicative of the secular change in the movement of the biological tissue is not limited to the graphs discussed above. For example, as shown in FIGS. 39 through 41, the movement information display control part 58 may cause the display part 6 to display an indicator bar IB' as the image indicative of the secular change in the movement of the biological tissue.

The indicator bar IB' above has its height varied depending on the displacement D, difference $\Sigma D$, velocity V, strain S, and correlation coefficient C regarding the biological tissue. When D<Dth, $\Sigma D$<$\Sigma Dth$, V<Vth and S<Sth, or when C>Cth, the indicator bar IB' appears the tallest as shown in FIG. 39. When D≥Dth, $\Sigma D$≥$\Sigma Dth$, V≥Vth and S≥Sth, or when C≤Cth, the indicator bar ID' appears shorter than the bar in FIG. 39, as illustrated in FIGS. 40 and 41.

Figure 41:
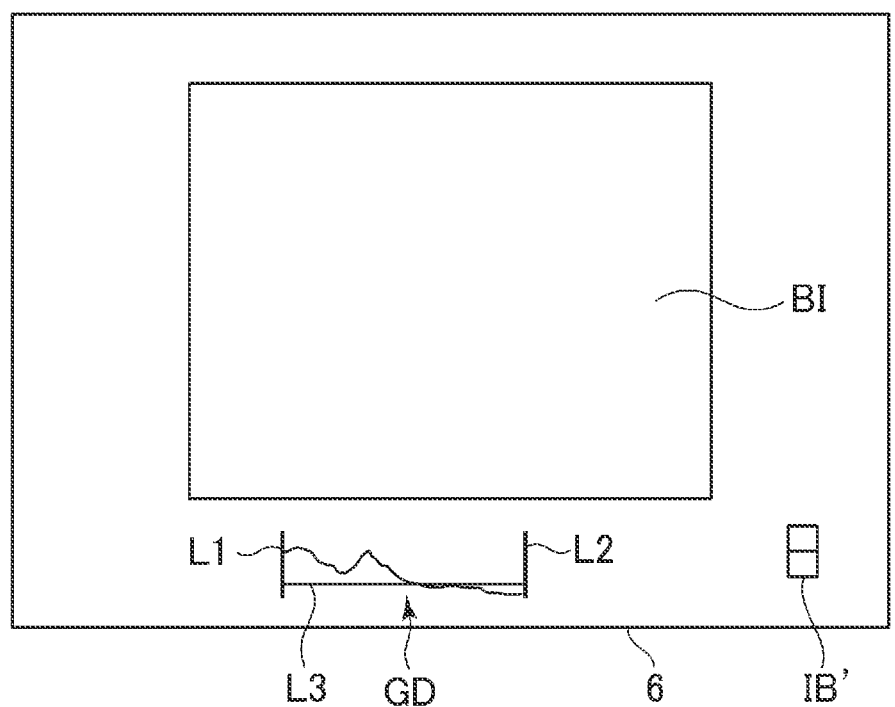
FIG. 41 is a diagram showing an indicator bar as another typical image indicative of a chronological change in the movement of a biological tissue.

The indicator bar IB' shown in FIG. 41 is displayed when D>Dth'(Dth'>Dth), $\Sigma D$>$\Sigma Dth'$($\Sigma Dth'$>$\Sigma Dth$), V>Vth' (Vth'>Vth) and S>Sth'(Sth'>Sth), or when C<Cth' (Cth'<Cth). The indicator bar IB' in FIG. 41 is the shortest bar displayed. The indicator IB shown in FIG. 40 is displayed when Dth≤D≤Dth', $\Sigma Dth$≤$\Sigma D$≤$\Sigma Dth'$, Vth≤V≤Vth' and Sth≤S≤Sth', or when Cth'≤C≤Cth. The indicator bar IB' in FIG. 40 has an intermediate height between the height of the indicator bar IB' in FIG. 39 and that of the indicator bar IB' in FIG. 41.

The indicator bar IB' may be displayed along with the above-described graph GD, G$\Sigma D$, GV, GS or GC. Alternatively, the indicator bar IB' alone may be displayed while the graph GD, G$\Sigma D$, GV, GS or GC is omitted. In FIGS. 39 through 41, the graph GD is displayed.

The indicator bar IB' may be displayed in different colors depending on bar height. For example, the shortest indicator bar IB' may be displayed in red, the tallest indicator bar ID' in blue, and the intermediate indicator bar ID' in yellow.

Figure 42:
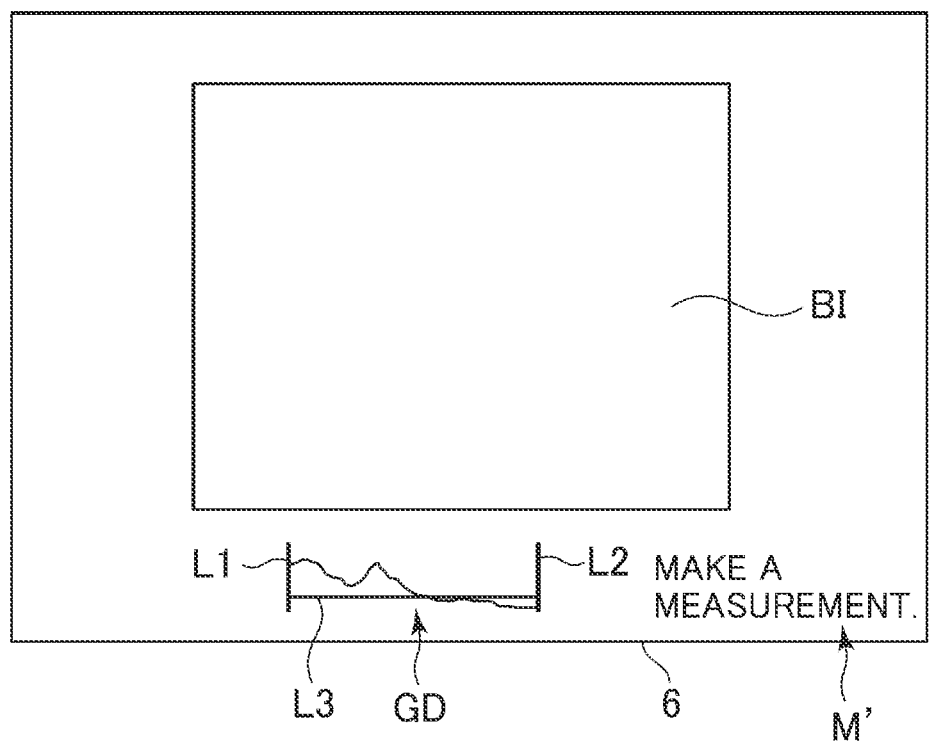
FIG. 42 is a diagram showing a display part displaying a graph indicative of a chronological change in displacement along with a message indicating that it is time to measure elasticity.

Also, when D<Dth, $\Sigma D$<$\Sigma Dth$, V<Vth and S<Sth, or when C>Cth, the movement information display control part 58 may cause the display part 6 to display a message M' indicating that it is time to transmit push pulses and measuring ultrasonic pulses, as shown in FIG. 42.

Further, when D<Dth, $\Sigma D$<$\Sigma Dth$, V<Vth and S<Sth, or when C>Cth, the control part 8 may cause the speaker 10 (see FIG. 15) to output a sound. This is a sound announcing that it is time to transmit push pulses and measuring ultrasonic pulses, such as a voice message or an alarm sound. The control part 8 causes the speaker 10 to output the sound based on the detection information from the movement detection part 57.

The correlation coefficient C may be obtained through a two-dimensional pattern matching process carried out on the corresponding region in two frames of the B-mode image data using correlation calculations.

Further, the flowcharts discussed above in conjunction with the embodiments are only examples and may be changed within the spirit and scope of the present invention.

Thus the scope of the invention should be determined by the appended claims and their legal equivalents, rather than by the examples given.

What is claimed is:

1. An ultrasonic diagnosis apparatus comprising:
an ultrasonic probe; and
a processor configured to:
control the ultrasonic probe to transmit ultrasonic pulses for detecting a movement of a biological tissue caused by a heartbeat or respiration;
execute a first program to implement a movement detection function for detecting the movement of the biological tissue based on echo data from the ultrasonic pulses for detecting the movement of the biological tissue, where detecting the movement includes detecting a displacement of the biological tissue;
execute a second program to determine a time period when the displacement of the biological tissue is less than a threshold value after detecting the movement of the biological tissue;
control the ultrasonic probe to transmit ultrasonic push pulses during the time period when the movement of the biological tissue is less than the threshold value; and
control the ultrasonic probe to transmit measuring ultrasonic pulses to the biological tissue after transmitting the ultrasonic push pulses, where the measuring ultrasonic pulses are adapted to detect a propagation velocity of a shear wave generated in the biological tissue by the ultrasonic push pulses.

2. An ultrasonic diagnosis apparatus according to claim 1, wherein the processor is further configured to display a first image showing a chronological change in the movement of the biological tissue.

3. An ultrasonic diagnosis apparatus according to claim 2, wherein the processor is further configured to display a second image indicating the transmission timing of the push pulses.

4. An ultrasonic diagnosis apparatus according to claim 1, wherein the processor is further configured to output a sound indicating that it is time to transmit the ultrasonic push pulses based on the detected displacement of the biological tissue with respect to the threshold value.

5. The ultrasonic diagnosis apparatus of claim 1, wherein the processor is configured to automatically control the ultrasonic probe to transmit the ultrasonic push pulses during the time period when the movement of the biological tissue is less than the threshold value.

* * * * *